United States Patent
Rule et al.

(10) Patent No.: US 10,973,692 B2
(45) Date of Patent: Apr. 13, 2021

(54) VISCOELASTIC WOUND CLOSURE DRESSING

(71) Applicant: 3M INNOVATIVE PROPERTIES COMPANY, Saint Paul, MN (US)

(72) Inventors: Joseph D. Rule, Woodbury, MN (US); Döne Demirgöz, Saint Paul, MN (US); Jennifer N. Hanson, Saint Paul, MN (US); James M. Jonza, Woodbury, MN (US); Gregory J. Anderson, Stillwater, MN (US); Raha A. Been, Wayzata, MN (US); David R. Holm, Hudson, WI (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 797 days.

(21) Appl. No.: 15/533,733

(22) PCT Filed: Dec. 10, 2015

(86) PCT No.: PCT/US2015/065016
§ 371 (c)(1),
(2) Date: Jun. 7, 2017

(87) PCT Pub. No.: WO2016/100089
PCT Pub. Date: Jun. 23, 2016

(65) Prior Publication Data
US 2019/0083321 A1      Mar. 21, 2019

Related U.S. Application Data

(60) Provisional application No. 62/094,116, filed on Dec. 19, 2014.

(51) Int. Cl.
*A61F 13/02* (2006.01)
*A61F 13/00* (2006.01)

(52) U.S. Cl.
CPC .... *A61F 13/00017* (2013.01); *A61F 13/0233* (2013.01); *A61F 13/0236* (2013.01); *A61F 13/0243* (2013.01); *A61F 13/00038* (2013.01)

(58) Field of Classification Search
CPC ............... A61F 13/00; A61F 13/00034; A61F 13/00038; A61F 13/0203; A61F 13/0206;
(Continued)

(56) References Cited

U.S. PATENT DOCUMENTS

RE24,906 E   12/1960  Ulrich
3,389,827 A   6/1968  Abere
(Continued)

FOREIGN PATENT DOCUMENTS

EP   1900512     3/2008
JP   2003052740  2/2003
(Continued)

OTHER PUBLICATIONS

US 8,115,048 B2, 02/2012, Gurtner (withdrawn)
(Continued)

*Primary Examiner* — Keri J Nelson
(74) *Attorney, Agent, or Firm* — 3M IPC

(57) ABSTRACT

A viscoelastic wound closure dressing. The dressing can include a viscoelastic backing having a first major surface configured to face skin when in use, a first end, a second end, and a middle section located between the first end and the second end. The wound closure dressing can further include a skin-contact adhesive on the first major surface of the viscoelastic backing adjacent the first end and the second end. A majority of the first major surface of the middle section can be free of the skin-contact adhesive. The viscoelastic backing can recover, at room temperature: (i) no more than 40% of its deformation after 10 seconds, after being strained to 50% elongation for 30 minutes, and (ii) at
(Continued)

least 70% of its deformation after 48 hours, after being strained to 50% elongation for 30 minutes.

14 Claims, 12 Drawing Sheets

(58) Field of Classification Search
CPC ............... A61F 13/0213; A61F 13/023; A61F 13/0233; A61F 13/0243
USPC .............................................. 602/43, 53, 58
See application file for complete search history.

(56) References Cited

U.S. PATENT DOCUMENTS

| | | | |
|---|---|---|---|
| 4,112,213 A | 9/1978 | Waldman | |
| 4,310,509 A | 1/1982 | Berglund | |
| 4,323,557 A | 4/1982 | Rosso | |
| 4,595,001 A | 6/1986 | Potter | |
| 4,737,410 A | 4/1988 | Kantner | |
| 5,098,421 A | 3/1992 | Zook | |
| 5,330,452 A | 7/1994 | Zook | |
| 5,762,620 A * | 6/1998 | Cartmell | A61B 17/085 602/42 |
| 6,180,544 B1 | 1/2001 | Jauchen | |
| 6,838,589 B2 | 1/2005 | Liedtke | |
| 6,881,875 B2 | 4/2005 | Swenson | |
| 6,977,323 B1 | 12/2005 | Swenson | |
| 7,005,143 B2 | 2/2006 | Abuelyaman | |
| 7,030,288 B2 | 4/2006 | Liedtke | |
| 7,223,468 B2 | 5/2007 | Yamamoto | |
| 7,612,248 B2 | 11/2009 | Burton | |
| 7,683,234 B2 | 3/2010 | Gurtner | |
| 7,981,136 B2 * | 7/2011 | Weiser | A61B 17/085 602/42 |
| 8,168,850 B2 | 5/2012 | Gurtner | |
| 8,183,428 B2 | 5/2012 | Gurtner | |
| 8,395,011 B2 * | 3/2013 | Zepeda | A61F 15/005 602/58 |
| 8,541,641 B2 | 9/2013 | Hirashima | |
| 8,604,266 B2 | 12/2013 | Spinelli | |
| 8,637,726 B2 | 1/2014 | Spinelli | |
| 2008/0233348 A1 | 9/2008 | Ishiwatari | |
| 2009/0187130 A1 | 7/2009 | Asmus | |
| 2010/0280428 A1 | 11/2010 | Widgerow | |
| 2011/0071448 A1 | 3/2011 | Margiotta | |
| 2012/0221044 A1 | 8/2012 | Archibald | |
| 2012/0277647 A1 | 11/2012 | Rastegar | |
| 2013/0237895 A1 | 9/2013 | Rastegar | |
| 2014/0228731 A1 | 8/2014 | Jackson | |
| 2014/0276324 A1 * | 9/2014 | Zepeda | A61F 13/0243 602/53 |

FOREIGN PATENT DOCUMENTS

| | | |
|---|---|---|
| JP | 2003053894 | 2/2003 |
| WO | WO 1998-26719 | 6/1998 |
| WO | WO 2010-056541 | 5/2010 |
| WO | WO 2010-056543 | 5/2010 |
| WO | WO 2010-056544 | 5/2010 |
| WO | WO 2014-021934 | 2/2014 |
| WO | WO 2015-094792 | 6/2015 |

OTHER PUBLICATIONS

Gurtner, "Improving Cutaneous Scar Formation by Controlling the Mechanical Environment", Annals of Surgery, 2011, vol. 254, No. 02, pp. 217-225.
International Search Report for PCT International Application No. PCT/US2015/065016, dated Mar. 11, 2016, 5 pages.
China National Intellectual Property Administration Search Report for CN201580069462.1, 3 pgs.

* cited by examiner

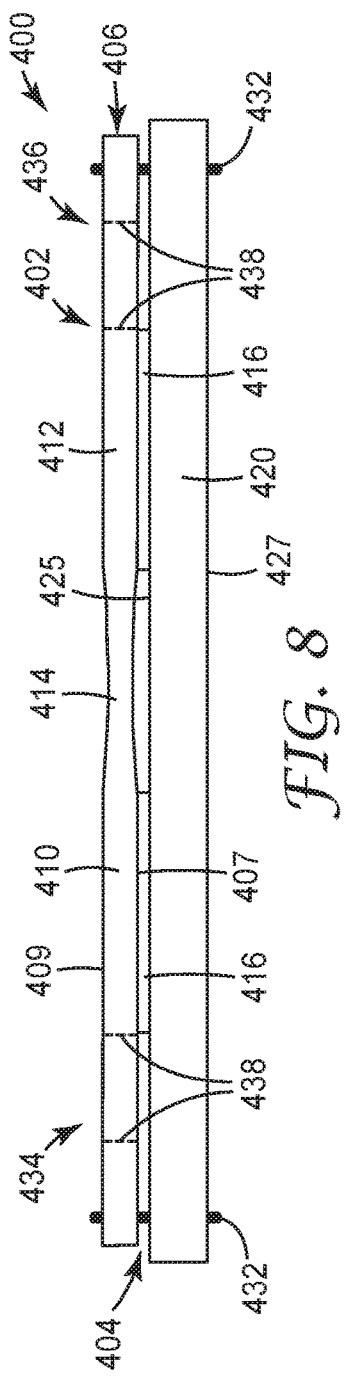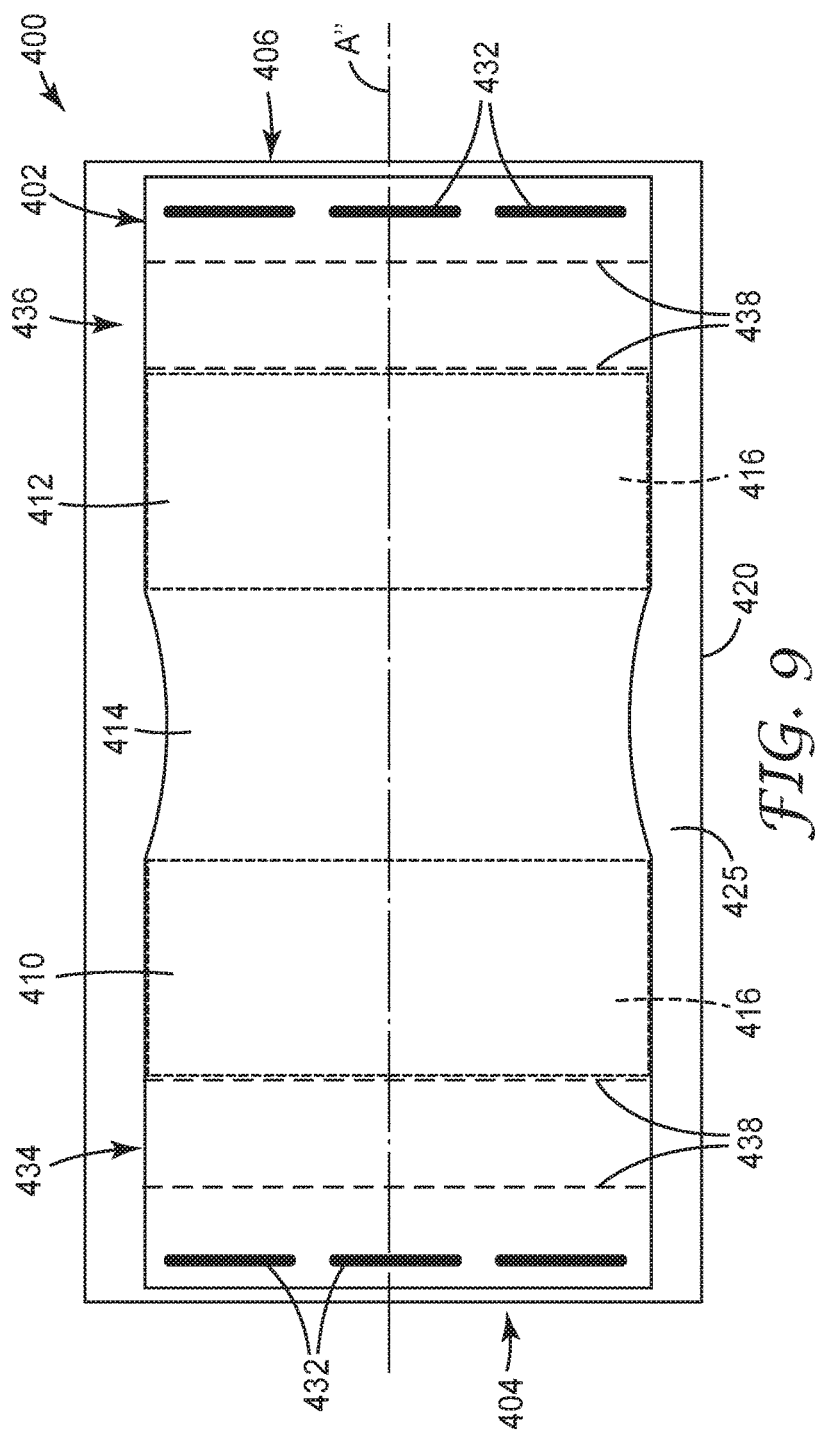

VISCOELASTIC WOUND CLOSURE DRESSING

CROSS REFERENCE TO RELATED APPLICATIONS

This application is a national stage filing under 35 U.S.C. 371 of PCT/US2015/065016, filed Dec. 10, 2015, which claims the benefit of U.S. Provisional Application No. 62/094,116, filed Dec. 19, 2014, the disclosures of which are incorporated by reference in their entirety herein.

FIELD

The present disclosure generally relates to a wound closure dressing comprising a viscoelastic backing, system comprising the wound closure dressing, and methods of using the wound closure dressing, e.g., to close wounds or maintain the wounds in a closed state.

BACKGROUND

Wound closure includes several types of technologies including one or more of sutures, staples, liquid adhesives, and dressings. Some existing wound closure devices require an application process that includes using fingers or forceps to appose skin edges as closely as possible. This manual apposition of the skin edges requires some skill to perform correctly.

In addition, some existing wound closure devices employ an elastic material that can be stretched across a wound, and the rebound of the elastic material can be exploited for wound closure. Some elastic wound closure devices can be applied to skin by (i) applying a first end of the elastic material to skin on one side of a wound, (ii) stretching the elastic material, and (iii) applying a second end of the elastic material to an opposite site of the wound. Such methods, however, require some skill to achieve proper stretching and application of the elastic material. Other elastic wound closure devices are pre-stretched and held in the pre-stretched state by a carrier. The entire assembly can then be applied to skin, and after the assembly has been applied to skin, the carrier can be removed to allow the elastic material to rebound. Such assemblies can be cumbersome and difficult to apply to skin as a whole, and can also require precise handling and control of the elastic material and carrier to ensure release of the elastic material at the desired time and in the desired location.

Furthermore, some existing wound closure devices employ shape memory materials that can be "locked" or "frozen" in a stretched configuration, e.g., by heating the material above its glass-transition temperature ($T_g$), stretching it, and then cooling the material to a temperature substantially below its $T_g$ to "lock" it in a meta-stable stretched configuration. When desired, the shape memory material can be heated to a temperature above its $T_g$ to at least partially recover its unstretched state. Such devices require maintaining the devices at a desired temperature (i.e., substantially below its $T_g$) to maintain the stretched configuration and then activating (e.g., thermally) the material to change it from its stretched configuration. That is, such wound closure devices can be applied to skin without a stretching force, but then must be activated or triggered to actively apply forces to a wound.

SUMMARY

Some aspects of the present disclosure provide a wound closure dressing including a viscoelastic backing comprising a first major surface configured to face skin when in use, a first end, a second end, and a middle section located between the first end and the second end. The viscoelastic backing can recover, at room temperature: (i) no more than 40% of its deformation after 10 seconds, after being strained to 50% elongation for 30 minutes, and (ii) at least 70% of its deformation after 48 hours, after being strained to 50% elongation for 30 minutes. The wound closure dressing can further include a skin-contact adhesive on the first major surface of the viscoelastic backing adjacent the first end and the second end, a majority of the first major surface of the middle section being free of the skin-contact adhesive.

Some aspects of the present disclosure provide a wound closure dressing kit comprising a first wound closure dressing of the present disclosure that is pre-stretched by a first percent elongation, and a second wound closure dressing of the present disclosure that is pre-stretched by a second percent elongation that is less than the first percent elongation.

Some aspects of the present disclosure provide a wound closure dressing system. Such a system can include a wound closure dressing of the present disclosure, with the viscoelastic backing in a pre-stretched configuration, and a support assembly. The wound closure dressing can be coupled to the support with the viscoelastic backing in the pre-stretched configuration, such that the pre-stretched configuration of the viscoelastic backing is maintained until the wound closure dressing is decoupled from the support.

Some aspects of the present disclosure provide a method of dressing a wound. Such a method can include providing a wound closure dressing system of the present disclosure, decoupling the wound closure dressing and the support assembly, and applying the wound closure dressing to skin after removing the wound closure dressing from the support.

Other features and aspects of the present disclosure will become apparent by consideration of the detailed description and accompanying drawings.

BRIEF DESCRIPTION OF THE DRAWINGS

FIG. 8 is a schematic side elevational view of a wound closure dressing system according to another embodiment of the present disclosure.

FIG. 9 is a schematic top plan view of the wound closure dressing system of FIG. 8.

DETAILED DESCRIPTION

Figure 1:
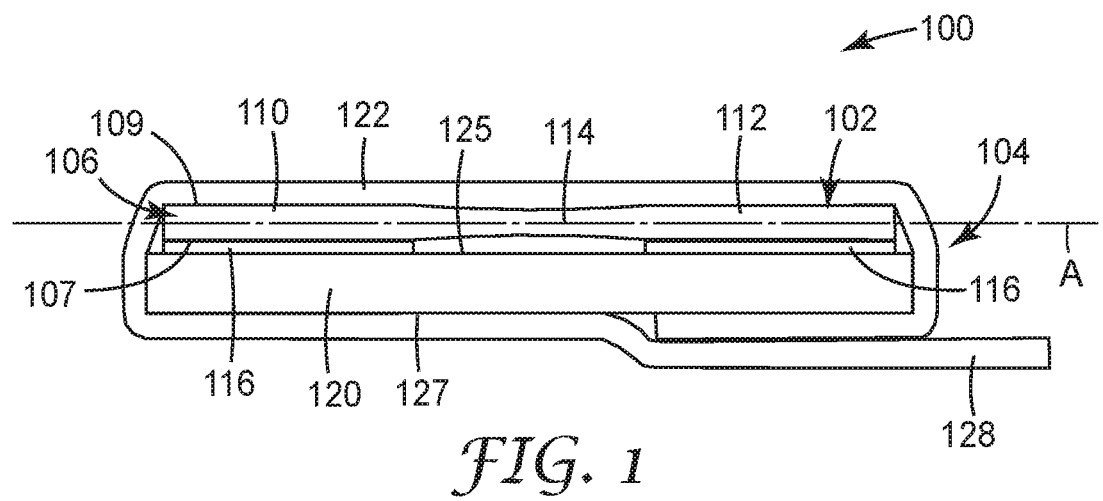
FIG. 1 is a schematic side elevational view of a wound closure dressing system according to one embodiment of the present disclosure, the wound closure dressing system including a wound closure dressing.

The present disclosure generally relates to wound closure dressings comprising viscoelastic backings that can be pre-stretched as desired, maintained in the pre-stretched configuration for as long as desired using one or more supports, removed from the supports, and then applied to skin (i.e., without the support). The viscoelastic backing can be designed such that the backing elastically recovers both at room temperature and at body surface temperature, but the viscous nature of the backing causes it to recover at a desired pace (i.e., slowly, compared to elastic materials).

Therefore, a stretched viscoelastic backing of the present disclosure can be briefly handled in the stretched state without requiring any forces be applied to the backing to maintain the stretched state. As a result, wound closure dressings of the present disclosure (or a portion thereof) can be pre-stretched during manufacturing by a controlled amount (e.g., to a controlled distance) and then stored and shipped in the pre-stretched state. At the point of use, the wound closure dressing can be applied to a wound without requiring a user to apply any stretching force to the dressing (i.e., the backing). Once applied, the backing viscoelastically recovers over a period of time to apply a closure force to the wound.

Furthermore, the viscoelastic backings of the wound closure dressings of the present disclosure can allow the stretching to be done in a manufacturing-type environment where better control is possible than in a clinical environment. For example, the overall percent elongation can be controlled with precision, where stretching by hand can be imprecise. Furthermore, a non-uniform stretch profile can be generated when the material is stretched by hand.

Thus, wound closure dressings of the present disclosure can enable less-skilled users or caregivers to safely and effectively apply the wound closure dressings because the dressings are provided in a pre-stretched configuration and can be briefly handled during application across a wound site without significant recovery.

Definitions

The term "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the terms "supported," and "coupled" and variations thereof are used broadly and encompass both direct and indirect supports and couplings.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The terms "room temperature" and "ambient temperature" are used interchangeably to mean a temperature in the range of 22° C. to 27° C.

The term "flexible" can generally be used to refer to a material that is drapable. That is, a section of material 5 cm×15 cm when held upright (long end up) folds over under its own weight to drop the opposite end to or below the holder, when performed at ambient conditions. The term "rigid" can generally be used to refer to a material that is essentially non-drapable. That is, a section of material 5 cm×15 cm when held upright (long end up) stands straight up with little or no deflection, when performed at ambient conditions. In some embodiments, rigid materials can show less than 20 degrees of deflection from vertical. "Semi-rigid" materials can be those that exhibit more than 20 degrees of deflection but whose opposite end does not drop below the holder.

The term "absorbent" refers to a material that is capable of absorbing fluids, particularly body fluids, and particularly, moderate to heavy amounts of body fluids, while retaining its structural integrity (i.e., remaining sufficiently intact such that it can perform the function of acting as an absorbent moist wound healing dressing, for example), and preferably its transparency.

The phrase "wound closure" is used to generally refer to applying forces necessary to at least partially close a wound, and/or to hold a wound closed. That is, in some embodiments, the wound closure dressings of the present disclosure can apply forces across a wound to perform the action of apposing two edges of skin that are separated, and in some embodiments, the wound closure dressings of the present disclosure can instead, or additionally, apply forces across a wound to hold or maintain two at least partially apposed edges of skin toward one another or together.

The term "transparent" and variations thereof, is used to refer to a material that, when applied to a patient (e.g., at a wound site), the area underlying the material can be sufficiently visualized through the material to permit visual inspection or observation of the area (e.g., wound) by a health care worker.

Figure 2:
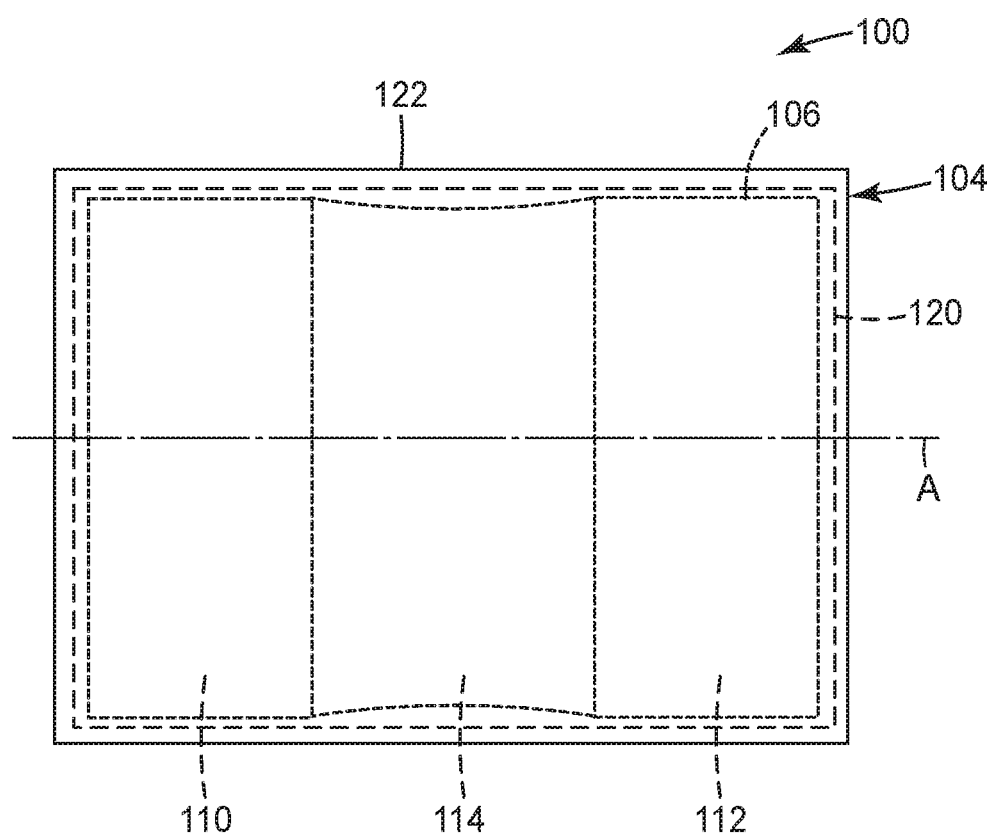
FIG. 2 is a schematic top plan view of the wound closure dressing system of FIG. 1.
Figure 3:
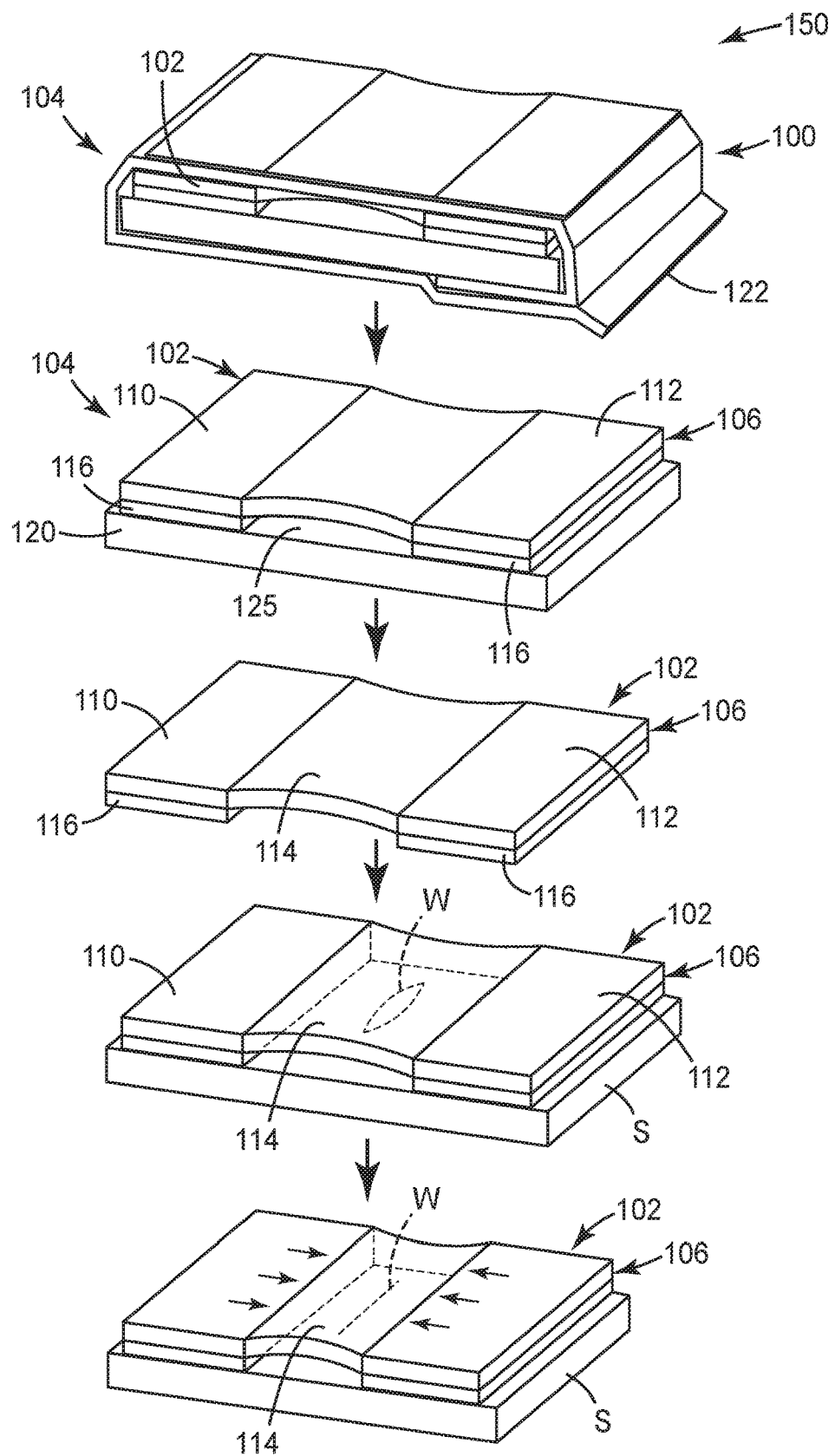
FIG. 3 illustrates a method of using the wound closure dressing system of FIGS. 1 and 2, shown in schematic top perspective views, to apply the wound closure dressing to skin.

FIGS. 1-3 illustrate a wound closure dressing system 100 and a wound closure dressing 102 according to one embodiment of the present disclosure. The wound closure dressing system 100 includes the wound closure dressing 102 and a support assembly 104 to which the wound closure dressing 102 is coupled to maintain a pre-stretched configuration, as described in greater detail below. FIG. 3 further illustrates a method of using the wound closure dressing system 100 to apply the wound closure dressing 102 to skin.

As shown in FIG. 1, the wound closure dressing 2 can include a viscoelastic backing 106 that has a first major surface 107 configured to face skin when in use, and a second major surface 109 opposite the first major surface 107 that is configured to face away from skin when in use. The viscoelastic backing 106 can further include a first (longitudinal) end 110, a second (longitudinal) end 112 opposite the first end 110, and a middle section 114 located (longitudinally) between the first end 110 and the second end 112.

As shown in FIGS. 1 and 2, the wound closure dressing 102 (or the backing 106) can include a longitudinal (or strain, or wound closure) axis A. As such, the first end 110 and the second end 112 are on opposite ends of the backing 106, with respect to the longitudinal axis. However, the viscoelastic backing 106 need not be elongated along the longitudinal axis A or having its greatest dimension along the longitudinal axis A. For example, in some embodiments, the wound closure dressing 102 may be circular or square, but the arrangement of the first end 110 and the second end 112 can at least partially define the longitudinal axis A of the wound closure dressing 102.

The wound closure dressing 102 can be configured to be removably secured to skin adjacent a wound site (i.e., on either, opposing sides of a wound site, such that the middle section 114 of the dressing 102 is positioned over the wound site) to shield the wound from endogenous and/or exogenous stress. In some embodiments, at least a portion of the viscoelastic backing 106, e.g., at least the middle section 114, can be transparent, such that the wound can be visualized through the viscoelastic backing 106 (e.g., through middle section 114) when the wound closure dressing 102 is adhered to skin and the middle section 114 is positioned over the wound site.

In some embodiments, the wound closure dressing 102 can be adhered to skin in the proximity of a wound by orienting the longitudinal axis A of the wound closure dressing 102 substantially perpendicularly with respect to an axis along with a wound is elongated. For example, in some cases, a wound may extend along an axis and may have a widest, gaping, portion at some point along that axis. In such cases, the wound closure dressing 102 can be adhered to the skin on either side of the wound, and particularly on either side of the widest portion of the wound and arranged such that the longitudinal axis of the wound closure dressing 102 is oriented substantially perpendicularly with respect to the wound axis, so as to provide a wound closure force to the widest portion of the wound.

Furthermore, in the case of incisions or wounds that are long or not straight, a series of smaller wound closure dressings 102 can be applied to follow the contour of the incision or wound. In such cases, the longitudinal axis A of each wound closure dressing 102 can be oriented substantially perpendicularly with respect to the wound axis at a particular location of the wound.

As shown in FIGS. 1 and 3, the wound closure dressing 102 can further include a skin-contact adhesive 116 on the first major surface 107 of the viscoelastic backing 106, at least adjacent the first end 110 and the second end 112. In some embodiments, the middle section 114 of the backing 106 can be free of the skin-contact adhesive 116. However, in some embodiments, the middle section 114 can include the skin-contact adhesive 116 patterned (e.g., pattern coated) on its first major surface 107, such that at least a majority of the first major surface 107 of the middle section 114 still includes significant open areas with no skin-contact adhesive 116. In some embodiments in which at least a majority of the first major surface 107 of the middle section 114 is free of the same skin-contact adhesive 116 that is present on the first end 110 and the second 112, the middle section 114 can include a different adhesive (e.g., a skin-contact adhesive), e.g., an adhesive that is less aggressive than the skin-contact adhesive 116.

Examples of various skin-contact adhesives that can be employed in wound closure dressings of the present disclosure are described in greater detail below in the 'Adhesives' section.

The skin-contact adhesive 116 need not be coextensive with the first major surface 107 in the regions of the first end 110 and the second 112. Rather, in some embodiments, the skin-contact adhesive 116 can be discontinuous (e.g., patterned), can extend not quite all the way to the edge or periphery of the backing 106, can have other suitable configurations, or a combination thereof.

The first end 110 of the backing 106, comprising the skin-contact adhesive 116 on the first major surface 107, can be configured to be secured (i.e., adhered) to skin on one side of a wound site by the skin-contact adhesive 116, and the second end 112, also comprising the skin-contact adhesive 116 on to the first major surface 107, can be configured to be secured (i.e., adhered) to skin on an opposite side of the wound site from the first end. The middle section 114, located between the first end 110 and the second end 112, can configured to be positioned over (i.e., above, in overlapping relationship with respect to) the wound site, but preferably not adhered to the wound site (i.e., when the first end 110 and the second end 112 are adhered to the skin on opposite sides of the wound site).

The present inventors discovered that when a skin-contact adhesive 116 (e.g., a relatively high-strength skin-contact adhesive 116) is placed in contact with wound edges, the wound edges become anchored to the viscoelastic backing 106, and the middle section 114 of the backing 106 then bridges the gap between the two wound edges. To fully close the wound, the middle section 114 of the backing 106 that bridges the wound gap would need to vanish entirely, which cannot occur through tensile contraction alone. Rather, in practice, the wound gap closes partially, but never completely. In contrast, when the middle section 114 is free of the skin-contact adhesive 116, the wound edges are not anchored to a particular point on the viscoelastic backing 106. As a result, during tensile contraction, the decrease in separation between the first end 110 and the second end 112 can exceed the width of the wound gap, and the wound can close completely.

As mentioned above, the viscoelastic backing 106 can be particularly useful for its ability to slowly recover (e.g., as compared to an elastic backing) when its pre-stretched configuration is released, i.e., when the wound closure dressing 102 is removed from the support 120. Such slow recovery can allow for facile handling of the wound closure dressing 102 and can allow sufficient time to properly position the wound closure dressing 102 relative to a wound and adhere it to the skin surrounding the wound, without the wound closure dressing 102 substantially rebounding.

The viscoelastic backing 106 can recover elastically after it is deformed by elongation from its fully relaxed state. In some embodiments, the fully relaxed state can be reached by raising the viscoelastic backing to a temperature of at least 40° C. in the absence of constraint or applied force. In some embodiments, after the viscoelastic backing is strained to 50% elongation for 30 minutes, it can be characterized by recovering (i.e., along the longitudinal axis A) at least 70% of its deformation after 48 hours at room temperature. In other words, after recovering 70% of its original 50% elongation, the overall elongation of the viscoelastic backing 106 would be 15% elongation.

In some embodiments, the viscoelastic backing 106 can be characterized by recovering (i.e., along the strain axis), no more than 40% of its deformation after 10 seconds (e.g., a useful amount of time to apply the wound closure dressing to skin) at room temperature after being strained to 50% elongation for 30 minutes; in some embodiments, no more than 35% of its deformation; in some embodiments, no more than 30% of its deformation; in some embodiments, no more than 25% of its deformation; in some embodiments, no more than 20% of its deformation; and in some embodiments, no greater than 10% of its deformation.

In some embodiments, the viscoelastic backing 106 can be further characterized by recovering at least 75% of its deformation after 48 hours at room temperature, after being strained to a 50% elongation for 30 minutes; in some embodiments, at least 80% of its deformation; in some embodiments, at least 85% of its deformation; in some embodiments, at least 90% of its deformation; in some embodiments, at least 95% of its deformation; and in some embodiments, 100% of its deformation.

In some embodiments, the wound closure dressing 102 can be formed by applying the skin-contact adhesive 116 to the first major surface 107 of the viscoelastic backing 106 (e.g., by coating or other suitable means of applying adhesive) adjacent the first end 110 and the second end 112 of the backing 106, and then the middle section 114 of the backing 106 located between the sections of skin-contact adhesive 116 can be strained to achieve the desired pre-stretched configuration. Straining of the backing 106 (and particularly, the middle section 114) can include heating the backing 106 to a desired temperature to facilitate uniform stretching.

The viscoelastic backing 106 can be formed of a variety of materials that meet the limitations of the present disclosure, including, but not limited to, polyurethanes, polyureas, polyethers, polyesters, poly(meth)acrylates, polyolefins, polyvinyl chloride, and combinations thereof.

To provide the desired viscoelasticity, the viscoelastic backing 106 can have a glass transition temperature near ambient temperature. For example, in some embodiments, the glass transition temperature of the viscoelastic backing 106 can be between 20° C. and 50° C., or between 25° C. and 45° C., or between 30° C. and 45° C. The glass transition temperature can be defined as the temperature of the peak of the tan delta signal in a dynamic mechanical analysis test.

In addition, to provide the desired recovery, in some embodiments, the viscoelastic backing 106 can have a stable rubbery plateau modulus. For example, the tensile modulus can be greater than 1 MPa at 80° C., or greater than 1 MPa at 100° C., or greater than 1 MPa at 130° C.

In some embodiments, the viscoelastic backing 106 can have a gel content of greater than 25%, or greater than 50%, or greater than 80%, when measured by extraction of soluble polymer in a suitable solvent (e.g., heated tetrahydrofuran).

In some embodiments, at least a portion of the viscoelastic backing 106 can be modified to improve breathability by including perforations or other cut-outs.

As described above, at least a portion of the viscoelastic backing 106 can be pre-stretched (i.e., oriented), or in a pre-stretched (or oriented) configuration or state. In some embodiments, only the middle section 114 of the backing 106, i.e., the section that is free of the skin-contact adhesive 116, is pre-stretched. This is shown schematically in FIGS. 1-3 by showing the middle section 114 as the only section of the backing 106 that is necked. In some cases, if the portion of the backing 106 (e.g., the first end 110 and/or the second end 112) that comprises the skin-contact adhesive 116 is stretched and then adhered to skin via the skin-contact adhesive 116, the backing 106 can pull on the skin as the backing 106 contracts. If the backing 106 contracts too strongly as it is adhered to the skin, opposing forces can develop in the skin over a small area, which can cause tension blisters to form in the skin under the dressing 102 in the area of the skin-contact adhesive 116. By stretching only the middle section 114 (i.e., the section free of the skin-contact adhesive 116), such potential drawbacks can be reduced or eliminated. In addition, by stretching only the middle section 114, adhesion of the wound closure dressing 102 to at least a portion of the support assembly 104 can be enhanced as well.

The viscoelastic backing 106 (and particularly, the middle section 114) can be pre-stretched to any desired % elongation to achieve desired results of the wound closure dressing 102. For example, in some embodiments, the viscoelastic backing 106 (and particularly, the middle section 114) can be pre-stretched (i.e., strained) to at least 10% elongation; in some embodiments, at least 20% elongation; in some embodiments, at least 30% elongation; in some embodiments, at least 40% elongation; in some embodiments, at least 50% elongation; in some embodiments, at least 60% elongation; in some embodiments, at least 70% elongation; in some embodiments, at least 80% elongation; in some embodiments, at least 90% elongation; and in some embodiments, 100% elongation. As described in greater detail below, in some embodiments, a first wound closure dressing 102 of the present disclosure can be applied to a wound (e.g., to provide substantial wound closing forces), and a second wound closure dressing 102 of the present disclosure can be applied to the same wound after the first wound closure dressing 102 is removed (e.g., to apply lesser closing forces but to maintain the wound closed). In such embodiments, the first wound closure dressing 102 can be deformed to a % elongation that is greater than the % elongation to which a second wound closure dressing 102 has been deformed. The % elongation of the first wound closure dressing 102 and the second wound closure dressing 102 can be specifically tuned for desired wound closing forces and for a specific application.

In some embodiments, the viscoelastic backing 106, or a portion thereof (e.g., the middle section 114) can be tested to see if it has been pre-stretched or is in a pre-stretched configuration. For example, if the viscoelastic backing 106 (or a portion thereof, such as the middle section 114) changes in length (i.e., contracts) by at least 10% after 24 hours at 30° C. from first removing the wound closure dressing 102 from any packaging or support, when left unconstrained, then it was pre-stretched.

In some embodiments, there may be overlap between the middle section 114 and the ends 110 and 112 of the viscoelastic backing 106. The first end 110 and the second end 112 of the viscoelastic backing 106 can be defined as ending wherein the skin-contact adhesive 116 ends and the middle section 114 can be defined as the portion of the viscoelastic backing 106 of which a majority is free of the skin-contact adhesive 116 (and in some embodiments, is free of the skin-contact adhesive 116). However, in some embodiments, the orientation (stretch) of the backing 106 may extend at least partially into the first end 110 and/or the second end 112. That is, in some embodiments, the backing 106 may include some orientation (i.e., from being pre-stretched) that extends beyond the middle section 114 and into one or both of the first and second ends 110 and 112, such that the orientation overlaps at least a portion of the skin-contact adhesive 116. Said another way, in some embodiments, the skin-contact adhesive 116 may be present on at least a portion of the first major surface 107 that extends into the middle section 114 of the backing 106. In such embodiments, the middle section 114 can still be described as having a majority of its first major surface 107 free of the skin-contact adhesive 116.

In some embodiments, more than 50% of the area of the first major surface 107 of the middle section 114 of the viscoelastic backing 106 is free of the skin-contact adhesive 116; in some embodiments, at least 60%; in some embodiments, at least 70%; in some embodiments, at least 75%; in some embodiments, at least 80%; in some embodiments, at least 85%; in some embodiments, at least 90%; and in some embodiments, at least 95%.

In some embodiments, the first major surface 107 of the middle section 114 of the viscoelastic backing 106 can be described as being "substantially free" of the skin-contact adhesive 116, which, in some embodiments, can refer to at least 750% of the area of the first major surface 107 of the middle section 114 being free of the skin-contact adhesive 116; in some embodiments, at least 80%; in some embodiments, at least 85%; in some embodiments, at least 90%; and in some embodiments, at least 95%.

In some embodiments, at least 80% of the first end 110 and/or the second end 112 is not oriented (stretched), i.e., does not contract when released according to the test described above; in some embodiments, at least 85% of the first end 110 and/or the second end 112 is not oriented; in some embodiments, at least 90%; in some embodiments, least 95%; and in some embodiments, at least 98%.

In some embodiments, the middle section 114 can be limited to a certain portion of the total length of the viscoelastic backing 106. For example, in some embodiments, the middle section 114 of the backing 106 has a length along the longitudinal axis A that is no greater than ⅓ of the total length of the viscoelastic backing 106; in some embodiments, no greater than ¼ of the total length of the viscoelastic backing 106.

In some embodiments, the wound closure dressing 102 can be maintained in a pre-stretched configuration by keeping the wound closure dressing 102 at a temperature below room temperature (e.g., at a temperature of about 5° C.).

In some embodiments, a support assembly, such as the support assembly 104 of FIGS. 1-3, can be used to maintain the wound closure dressing 102 in a pre-stretched configuration, e.g., during manufacturing, packaging, storage, and/or handling. In some embodiments, as shown in FIGS. 1-3, the support assembly 104 can include a support 120 that can be more rigid than the viscoelastic backing 106 and to which the wound closure dressing 102 can be coupled when in its pre-stretched configuration to maintain, or substantially maintain, the pre-stretched configuration for as long as desired. That is, in some embodiments, the viscoelastic backing 106 can be flexible (i.e., less rigid than the support 120), and the support 120 can be at least semi-rigid or rigid (i.e., more rigid than the viscoelastic backing 106).

In some embodiments, the wound closure dressing 102 can be coupled to at least a portion of the support 120 via the skin-contact adhesive 116. For example, as shown in FIG. 1, in some embodiments, the support 120 can include a first major surface 125 to which the wound closure dressing 102 can be coupled via the skin-contact adhesive 116, and a second major surface 127 opposite the first major surface 125.

In some embodiments, the support 120, i.e., at least a portion of the first major surface 125 of the support 120, can be used in place of a release liner and can provide release characteristics to the skin-contact adhesive 116 to facilitate removal of the wound closure dressing 102 from the support 120 when desired. However, the release characteristics of the support 120 can be configured such that the first major surface 125 (or a portion thereof) also provides sufficient adhesion for the skin-contact adhesive 116 to maintain the viscoelastic backing 106 (or at least the middle section 114 thereof) in its pre-stretched configuration, without allowing for substantial contraction of the backing 106 prior to use. The adhesion between the skin-contact adhesive 116 and the support 120 (as well as the adhesion between the skin-contact adhesive 116 and the viscoelastic backing 106) in such embodiments can be tuned to provide this balance.

In some embodiments, the average peel strength between the skin-contact adhesive 116 and the support 120, e.g., when tested according to the 180° Peel Test Method described in the Examples below, can be at least 1.0 N/cm; in some embodiments, at least 1.2 N/cm; and in some embodiments, at least 1.4 N/cm. In some embodiments, the average peel strength between the skin-contact adhesive 116 and the support 120 can be no greater than 4 N/cm; in some embodiments, no greater than 3 N/cm; and in some embodiments, no greater than 2 N/cm.

In some embodiments, the entire first end 110 and second 112 can be adhered to the first major surface 125 of the support 120, as shown in FIGS. 1 and 3. However, in some embodiments, the wound closure dressing 102 can include one or more release liners positioned over at least a portion of the skin-contact adhesive 116, e.g., over at least a portion of the skin-contact adhesive 116 on the first end 110 and/or over at least a portion of the skin-contact adhesive 116 on the second end 112. In such embodiments, the covered portions of the skin-contact adhesive 116 will not adhere to the support 120 and can facilitate decoupling the wound closure dressing 102 and the support 120 by allowing the non-adhered portion of the first end 110 and/or the second end 112 to function as a tab.

As further shown in FIGS. 1-3, in some embodiments, the support assembly 104 can further include an overwrap 122. The overwrap 122 is shown by way of example only as one way of further coupling the wound closure dressing 102 to the support 120 and further supporting the wound closure dressing 102 in its pre-stretched state. As shown in FIGS. 1 and 3, the overwrap 122 can be configured to be positioned over or around at least a portion of the wound closure dressing 102 and the support 120. For example, as shown in FIG. 1, in some embodiments, the overwrap 122 can include a first end that can be coupled (e.g., adhered) to the second major surface 127 of the support 120 (i.e., opposite the wound closure dressing 102), and then can be dimensioned to be wrapped up and over one side or edge of the support 120 and the wound closure dressing 102, down along the wound closure dressing 102 (e.g., along the longitudinal axis A, e.g., adjacent the second major surface 109 of the viscoelastic backing 106), then down around an opposite side or edge of the support 120 and the wound closure dressing 102, then down along the second major surface 127 of the support 120, and finally overlapping the first end of the overwrap 122 adjacent the second major surface 127 of the support 120, optionally forming a tab 128 for easy removal. As shown in FIGS. 2 and 3, in some embodiments, the overwrap 122 can further be sized so as to overhang the edges, or periphery, of the wound closure dressing 102 and the support 120.

In some embodiments, in addition to, or instead of the overwrap 122, the wound closure dressing 102 can be further coupled to the support 120 by one or more fasteners. That is, in some embodiments, the support assembly 104 can include one or more fasteners. One example of a wound closure dressing of the present disclosure that employs fasteners is described in greater detail below with respect to FIGS. 8 and 9.

Some embodiments of the present disclosure can include a wound closure dressing kit comprising more than one wound closure dressing 102. For example, in some embodiments, such a kit can include a first wound closure dressing 102 (or first wound closure dressing system 100 comprising a first wound closure dressing 102) that has been pre-stretched by a first amount (i.e., a first percent elongation), and a second wound closure dressing 102 (or second wound closure dressing system 100 comprising a second wound closure dressing 102) that has been pre-stretched by a second amount (i.e., a second percent elongation), with the first amount being greater than the second amount.

For example, the first amount of pre-stretch can be configured to apply sufficient forces to skin adjacent a wound site to at least partially close the wound (e.g., to be applied to a wound for the first 1-3 days), and the second amount of pre-stretch (which can be less than the first amount) can be configured to apply sufficient forces to the skin to hold the wound closed, e.g., to reduce scar formation. In such embodiments, the second wound closure dressing 102 can be applied second to the wound, after the first wound closure dressing 102 has been used. The first and second wound closure dressings 102 need not be identical, but rather can be formed of different materials. In addition, in some embodiments, the first and second wound closure dressings 102 can be coupled to the same support assembly 104, but in other embodiments, the first wound closure dressing 102 can be coupled to a first support assembly 104, and the second wound closure dressing 102 can be coupled to a second support assembly 104 that is different from the first support assembly 104.

In some embodiments, the support 120 can be formed of a variety of materials, including, but not limited to, polymeric materials, cellulosic materials (like cardboard or wood), glass, metal, other suitably rigid materials, or a combination thereof. In some embodiments, the support 120 can have a sufficient thickness to provide sufficient stiffness. For example, in some embodiments, the support 120 can have a thickness that is greater than 0.1 mm, in some embodiments, greater than 0.2 mm, and in some embodiments, greater than 0.5 mm. In some embodiments, the support 120 can be made of a polyolefin sheet including polypropylene, polyethylene, or copolymers thereof. In some embodiments, the support 120 can be made of a cardboard sheet, e.g., with a surface treatment to provide release properties described above.

In some embodiments, the overwrap 122 can be formed of a variety of materials, including, but not limited to, pressure-sensitive adhesive films or tapes, hot-melt adhesive coated films or tapes, curable adhesive coated tapes, other suitable materials, or a combination thereof. In some embodiments, the overwrap 122 can adhere to the support 120 and the viscoelastic backing 106. The adhesion of the overwrap 122 to the support 120 and the viscoelastic backing 106 can be designed to provide sufficiently high adhesive strength to support the wound closure dressing 102 in its pre-stretched state, but sufficiently low adhesive strength to allow removal of the overwrap 122 from the wound closure dressing 102 without deforming or damaging the dressing 102. In some cases, an overwrap 122 can include a silicone-based pressure-sensitive adhesive. In some cases, an overwrap 122 can include paper coated with ethylene vinyl acetate or a hot-melt adhesive.

In some embodiments, the wound closure dressing 102 can further include one or more carriers that can be coupled to the second major surface 109 of the viscoelastic backing 106 and which can provide stability to the backing 106 (e.g., to the first end 110 and/or the second end 112) during handling and application of the wound closure dressing 102. Examples of embodiments of wound closure dressings of the present disclosure that employ carriers are described in greater detail below with respect to FIGS. 10-15.

In some embodiments, the wound closure dressing 102 can further include one or more absorbent layers positioned to absorb fluid (e.g., wound exudate) and/or to inhibit contamination of the wound. Such absorbent layers, for example, can be coupled to the first major surface 107 of the middle section 114 of the backing 106 that is configured to be positioned over a wound site. Examples of wound closure dressings of the present disclosure employing such absorbent layers are described in greater detail below with respect to FIGS. 4-7.

A method of dressing or closing a wound will now be described with respect to FIG. 3, which illustrates a method 150 of using the wound closure dressing system 100 of FIGS. 1 and 2.

As shown in FIG. 3, the wound closure dressing system 100 can be provided with the wound closure dressing 102 coupled to the support assembly 104 in a pre-stretched configuration. Particularly, the middle section 114 of the viscoelastic backing 106 is provided in a pre-stretched configuration, and that pre-stretched configuration is maintained by the support assembly 104.

Then, the wound closure dressing 102 can be decoupled from the support assembly 104. Particularly, as shown in FIG. 3, the overwrap 122 can be removed from the wound closure dressing 102 and the support 120. After the overwrap 122 is removed, there is a possibility that the viscoelastic backing 106 can begin to recover at least slightly from its pre-stretched configuration. However, as shown, after the overwrap 122 is removed, the wound closure dressing 102 still remains adhered to the first major surface 125 of the support 120 via the skin-contact adhesive 116 (i.e., which adheres the first end 110 and the second end 112 to the support 120). As a result, the adhesion between the skin-contact adhesive 116 and the support 120 can be tuned to minimize recovery of the viscoelastic backing 106 while the viscoelastic backing 106 is still adhered to the support 120.

As further shown in FIG. 3, the wound closure dressing 102 (which may additionally include one more absorbent layers, carriers, etc.) can then be removed from the support 120 by peeling the skin-contact adhesive 116 from the first major surface 125 of the support 120. The first end 110 and the second end 112 can be removed sequentially from the support 120. Because of the viscoelastic properties of the viscoelastic backing 106, the viscoelastic backing 106 does not immediately recover from its pre-stretched elongation after the support 120 is removed, and a user has time to properly apply the wound closure dressing 102.

The wound closure dressing 102 (i.e., the skin-contact adhesive 116) can then be applied to skin S. Particularly, the first end 110 of the viscoelastic backing 106 can be applied to skin S adjacent a first side of a wound site W, and the second end 112 of the viscoelastic backing 106 can be applied to skin S adjacent a second side of the wound site W, opposite the first side, such that the middle section 114 is positioned over (i.e., in overlapping relationship with) the wound site W, but not adhered to the wound site W, as shown in the fourth step of FIG. 3.

The wound closure dressing 102, particularly, the viscoelastic backing 106, and more particularly, the pre-stretched middle section 114, can then be allowed to at least partially recover its deformation, while the wound closure dressing 102 remains adhered to the skin S, such that the wound closure dressing 102 exerts forces on the skin S, as shown by the arrows in the fifth step shown in FIG. 3, to at least partially close the wound and/or to at least partially maintain the wound closed.

Additional exemplary embodiments of wound closure dressings of the present disclosure will now be described with respect to FIGS. 4-7. FIGS. 4-7 illustrate various wound closure dressings of the present disclosure, wherein like numerals represent like elements. The wound closure dressings of FIGS. 4-7 share many of the same elements, features, and functions as the wound closure dressing 102 described above with respect to FIGS. 1-3. Reference is made to the description above accompanying FIGS. 1-3 for a more complete description of the features and elements (and alternatives to such features and elements) of the embodiments illustrated in FIGS. 4-7. Any of the features described above with respect to FIGS. 1-3 can be applied to the embodiments of FIGS. 4-7, and vice versa.

Figure 4:
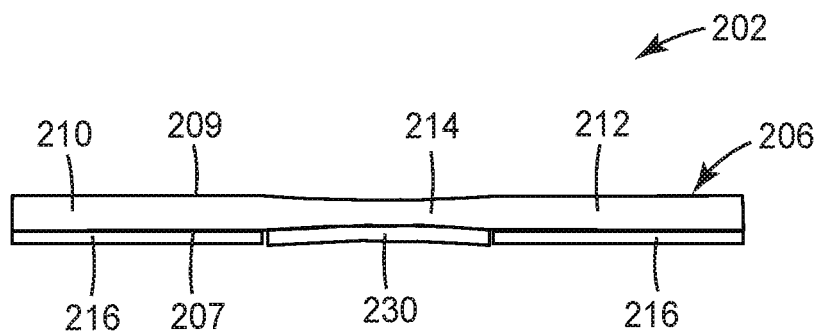
FIG. 4 is a schematic side elevational view of a wound closure dressing according to another embodiment of the present disclosure.
Figure 5:
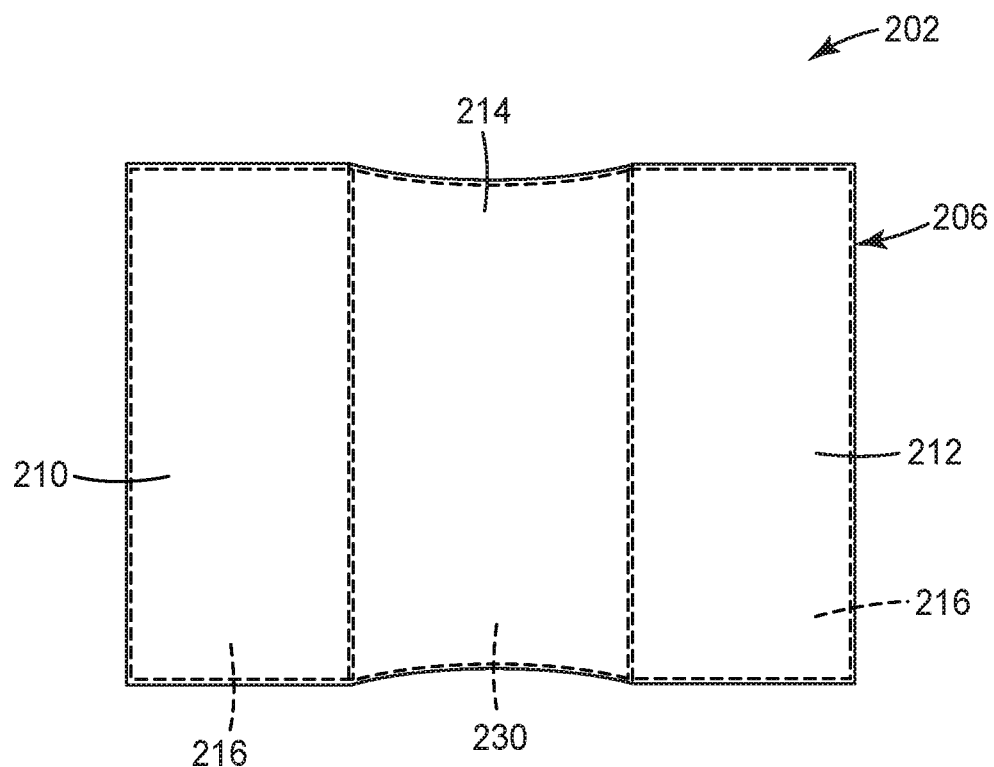
FIG. 5 is a schematic top plan view of the wound closure dressing of FIG. 4.

FIGS. 4 and 5 illustrate a wound closure dressing 202 according to another embodiment of the present disclosure. The wound closure dressing 202 includes a viscoelastic backing 206 having a first major surface 207, a second major surface 209, a first end 210, a second end 212, and a middle section 214; and a skin-contact adhesive 216 on the first major surface 207 of the first end 210 and the second end 212 of the viscoelastic backing 206. By way of example, the viscoelastic backing 206 is illustrated in FIGS. 4 and 5 with the middle section 214 in a pre-stretched configuration.

The wound closure dressing 202 of FIGS. 4 and 5 is substantially the same as the wound closure dressing 102 of FIGS. 1-3, except that the wound closure dressing 202 includes an absorbent layer 230. As shown in FIGS. 4 and 5, in some embodiments, the absorbent layer 230 can be coupled to at least a portion of the first major surface 207 of the middle section 214, such that the absorbent layer 230 can be positioned over a wound site when the wound closure dressing 202 is adhered to skin. Such an absorbent layer 230 can be configured to absorb fluids (e.g., wound exudate), and can also at least partially protect the wound site from ambience, e.g., to seal out microbial contamination and/or debris. The absorbent layer 230 can be applied to the middle section 214 before or after the middle section 214 is pre-stretched.

Generally, the absorbent layer 230 does not have a high adhesive strength for at least the reasons outlined above with respect to keeping the middle section free of skin-contact adhesive. However, in some embodiments, the absorbent layer 230 can include a latent adhesive material that does not initially have aggressive adhesion, but can subsequently be triggered to have increased adhesion due to light exposure, air exposure, moisture, other suitable stimuli, or combinations thereof. Alternatively, the absorbent layer 230 can have low adhesive strength, but can retain the ability to seal the wound from contamination and infection. For example, in some embodiments, the absorbent layer 230 can include a clear absorbent material available under the trade designation 3M™ TEGADERM™ from 3M Company. In such embodiments, the wound closure dressing 202 can serve the role of providing a covering to a 3M™ TEGADERM™ clear absorbent material, in addition to its wound closure role. In other embodiments, the absorbent layer 230 can include a hydrogel, such as a pressure-sensitive adhesive hydrogel (e.g., a silicone pressure-sensitive adhesive hydrogel). Other examples of absorbent layer materials and features are described in greater detail below and can be employed in any of the wound closure dressings of the present disclosure.

As shown in FIGS. 4 and 5, in some embodiments, the absorbent layer 230 can be substantially coextensive with the middle section 214, however, this need not be the case. In some embodiments, the absorbent layer 230 can be applied to (e.g., coated on) only a portion of the first major surface 207 of the middle section 214; and in some embodiments, the absorbent layer 230 can be patterned on at least a portion of the first major surface 207 of the middle section 214, such that portions of the first major surface 207 of the middle section 214 remain exposed, yet the absorbent layer 230 can still provide a seal.

As shown schematically in FIG. 4, in some embodiments, the absorbent layer 230 can have a thickness that is about equal to the skin-contact adhesive 216 on the first end 210 and the second 212. However, in some embodiments, the absorbent layer 230 can be thinner or thicker than the skin-contact adhesive 216 on the first end 210 and the second end 212.

In some embodiments, the absorbent layer 230 can be transparent, such that the wound can be visualized through the middle section 214 when the wound closure dressing 202 is adhered to skin and the middle section 214 is positioned over the wound site. Transparency of the absorbent layer 230 can be particularly useful in embodiments in which the absorbent layer 230 covers a majority of the first major surface 207 of the middle section 214, as shown in FIG. 5.

While the absorbent layer 230 is shown as being a single, continuous layer applied to the middle section 214, in some embodiments, the middle section 214 can instead include two overlapping and interdigitated absorbent layers 230. That is, in some embodiments, the middle section 214 can include (i) a first absorbent layer 230 having a first longitudinal end coupled to the middle section 214 and a second opposite longitudinal end that is free, i.e., not coupled to the middle section 214; and a (ii) a second absorbent layer 230 having a first longitudinal end coupled to the middle section 214 and a second opposite longitudinal end that is free, i.e., not coupled to the middle section 214. The free ends of the absorbent layers 230 can overlap one another, such that they can slide over one another when the backing 206 (e.g., the middle section 214) is stretched (perhaps to a point where they no longer overlap), and can slide back over one another as the backing 206 recovers.

Figure 6:
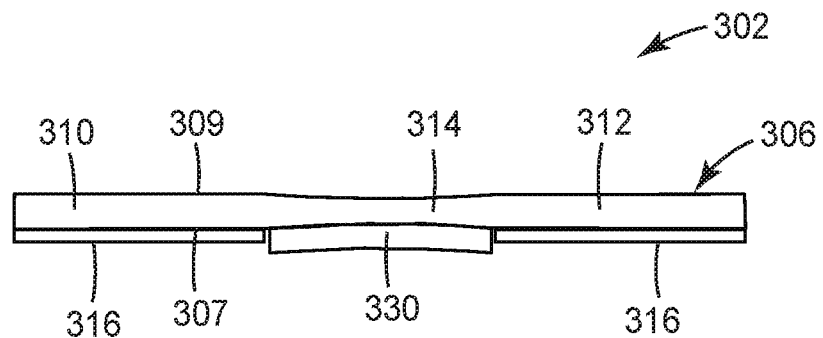
FIG. 6 is a schematic side elevational view of a wound closure dressing according to another embodiment of the present disclosure.
Figure 7:
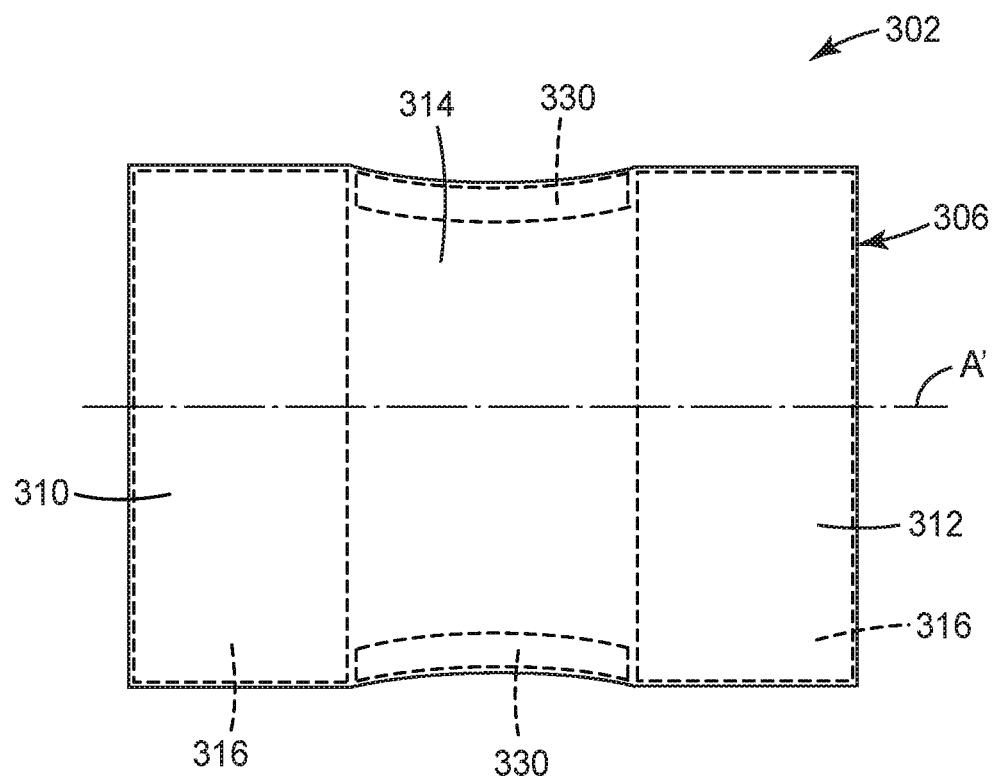
FIG. 7 is a schematic top plan view of the wound closure dressing of FIG. 6.

FIGS. 6 and 7 illustrate a wound closure dressing 302 according to another embodiment of the present disclosure. The wound closure dressing 302 includes a viscoelastic backing 306 having a first major surface 307, a second major surface 309, a first end 310, a second end 312, and a middle section 314; and a skin-contact adhesive 316 on the first major surface 307 of the first end 310 and the second end 312 of the viscoelastic backing 306. By way of example, the viscoelastic backing 306 is illustrated in FIGS. 6 and 7 with the middle section 314 in a pre-stretched configuration.

The wound closure dressing 302 of FIGS. 6 and 7 is substantially the same as the wound closure dressing 102 of FIGS. 1-3 and the wound closure dressing 202 of FIGS. 4 and 5, except that the wound closure dressing 302 includes two peripheral absorbent layers 330 located adjacent side or lateral edges of the middle section 314—e.g., lateral edges that extend generally along a longitudinal axis A' of the wound closure dressing 302 and are spaced a distance from the longitudinal axis A'. Such absorbent layers 330 can include any of the features and elements described above with respect to the absorbent layer 230 of FIGS. 4 and 5 and/or any of the features and elements described below in the 'Absorbent Layers' section.

As shown in FIGS. 6 and 7, in some embodiments, the absorbent layers 330 can be coupled to at least a portion of the first major surface 307 of the middle section 314, such that the absorbent layer 330 can be positioned adjacent a wound site when the wound closure dressing 302 is adhered to skin. By positioning the absorbent layers 330 toward the lateral sides of the middle section 314, a central portion (e.g., a majority) of the first major surface 307 of the middle section 314 can remain exposed to the wound site. In addition, while the absorbent layers 330 can be transparent, they need not be, particularly in embodiments in which the majority of the middle section 314 remains exposed, such that the wound site can still be observed via the middle section 314.

The laterally or peripherally located absorbent layers 330 can still provide the function of absorbing fluids and/or sealing the wound site from the environment (e.g., contamination and/or debris), while maintaining a substantial portion of the middle section 314 spaced from the wound and free of adhesive so as not to inhibit effective wound closure.

As shown schematically in FIG. 6, in some embodiments, the absorbent layers 330 can have a thickness that is greater than that of the skin-contact adhesive 316 on the first end 310 and the second 312. However, in some embodiments, the absorbent layers 330 can be thinner or have the same thickness as that of the skin-contact adhesive 316 on the first end 310 and the second end 312.

While the absorbent layers 330 are shown as being single, continuous layers applied to each lateral side of the middle section 314, in some embodiments, each lateral side of the middle section 314 instead include two overlapping and interdigitated absorbent layers 330. That is, in some embodiments, each lateral side of the middle section 314 can include (i) a first absorbent layer 330 having a first longitudinal end coupled to the middle section 314 and a second opposite longitudinal end that is free, i.e., not coupled to the middle section 314; and a (ii) a second absorbent layer 330 having a first longitudinal end coupled to the middle section 314 and a second opposite longitudinal end that is free, i.e., not coupled to the middle section 314. The free ends of the absorbent layers 330 can overlap one another, such that they can slide over one another when the backing 306 (e.g., the middle section 314) is stretched (perhaps to a point where they no longer overlap), and can slide back over one another as the backing 306 recovers.

Some wound closure dressings of the present disclosure can employ a combination of the absorbent layer 230 of FIGS. 4 and 5 and the absorbent layers 330 of FIGS. 6 and 7.

Additional exemplary embodiments of wound closure dressing systems and wound closure dressings of the present disclosure will now be described with respect to FIGS. 8-15. FIGS. 8-15 illustrate various wound closure dressing systems of the present disclosure, wherein like numerals represent like elements. The wound closure dressing systems of FIGS. 8-15 share many of the same elements, features, and functions as the wound closure dressing system 100 described above with respect to FIGS. 1-3. Reference is made to the description above accompanying FIGS. 1-3 for a more complete description of the features and elements (and alternatives to such features and elements) of the embodiments illustrated in FIGS. 8-15. Any of the features described above with respect to FIGS. 1-3 can be applied to the embodiments of FIGS. 8-15, and vice versa. In addition, any of the features of the wound closure dressings of FIGS. 1-7 can be employed in the wound closure dressings and wound closure dressing systems of FIGS. 8-15, including the wound closure dressings of FIGS. 4-7.

FIGS. 8 and 9 illustrate a wound closure dressing system 400 and wound closure dressing 402 according to another embodiment of the present disclosure. The wound closure dressing system 400 includes the wound closure dressing 402 and a support assembly 404. The wound closure dressing 402 includes a viscoelastic backing 406 having a first major surface 407, a second major surface 409, a first end 410, a second end 412, and a middle section 414; and a skin-contact adhesive 416 on the first major surface 407 of the first end 410 and the second end 412 of the viscoelastic backing 406. By way of example, the viscoelastic backing 406 is illustrated in FIGS. 8 and 9 with the middle section 414 in a pre-stretched configuration.

As shown, the support assembly 404 includes a support 420 having a first major surface 425 and a second major surface 427, and the wound closure dressing 402 is adhered to the first major surface 425 of the support 420 via the skin-contact adhesive 416 to maintain the wound closure dressing 402 (i.e., the middle section 414 of the viscoelastic backing 406) in a pre-stretched configuration.

The main difference between the wound closure dressing system 400 and the wound closure dressing system 100 of FIGS. 1-3 is that the support assembly 404 does not include an overwrap. Rather, the support assembly 404 includes one or more fasteners 432 positioned to further couple at least a portion of the viscoelastic backing 406 to the support 420. By way of example, the viscoelastic backing 406 includes a first extension 434 that extends longitudinally beyond the first end 410, and a second extension 436 that extends longitudinally beyond the second end 412. The first extension 434 and the second extension 436 can thus be secured to the support 420 by the one or more fasteners 432 without damaging or effectively any useful portion of the backing 406 or wound closure dressing 402.

In the embodiment of FIGS. 8 and 9, the first extension 434 and the second extension 436 of the viscoelastic backing 406 are shown as being free of the skin-contact adhesive 416, which can facilitate separating the useful portion of the backing 406 from the fastener 432. However, in some embodiments, the skin-contact adhesive 416 can be present on at least a portion of at least one of the first extension 434 and the second extension 436.

As shown in FIGS. 8 and 9, in some embodiments, the first extension 434 and the second extension 436 of the backing 406 can include one or more perforated lines 438, which can be oriented substantially transverse or laterally (i.e., substantially perpendicularly) with respect to a longitudinal axis A" of the wound closure dressing 402. Particularly, each perforated line 438 can be present in the first and second extension 434 and 436 and located internally with respect to the fastener 432.

In the embodiment illustrated in FIGS. 8 and 9, each of the first extension 434 and the second extension 436 include two perforated lines 438. As such, the wound closure dressing 402 can be removed from the support assembly 404 when desired by first tearing out the portion of each of the first and second extensions 434 and 436 located between the perforated lines 438, and then peeling the skin-contact adhesive 416 from the first major surface 425 of the support 420. Alternatively, if each of the first and second extensions 434 and 436 include just one perforated line 438, the backing 406 can be decoupled from the fastener(s) 432 by tearing along the perforated line 438.

The fasteners 432 of the support assembly 404 are shown as including a series of staples along each of the first extension 434 and the second extension 436 of the backing 406. However, the fasteners 432 can include any of a variety of fasteners, including, but not limited to, staples, stitches, nails, screws, rivets, brads, crimps, clamps, hook-and-loop-type fasteners, welding (e.g., sonic (e.g., ultrasonic) welding), thermal bonds or seals, other suitable fasteners, or a combination thereof.

Figure 10:
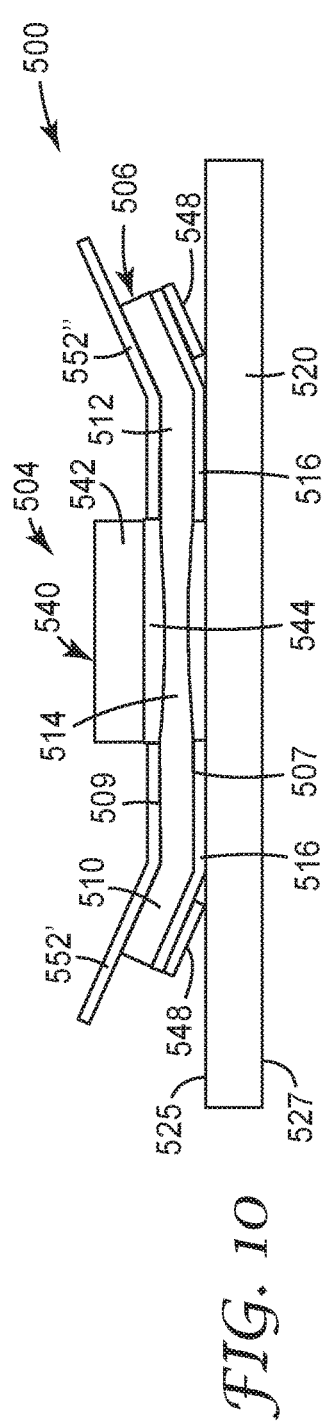
FIG. 10 is a schematic side cross-sectional view of a wound closure dressing system according to another embodiment of the present disclosure, the wound closure dressing system comprising a wound closure dressing.
Figure 11:
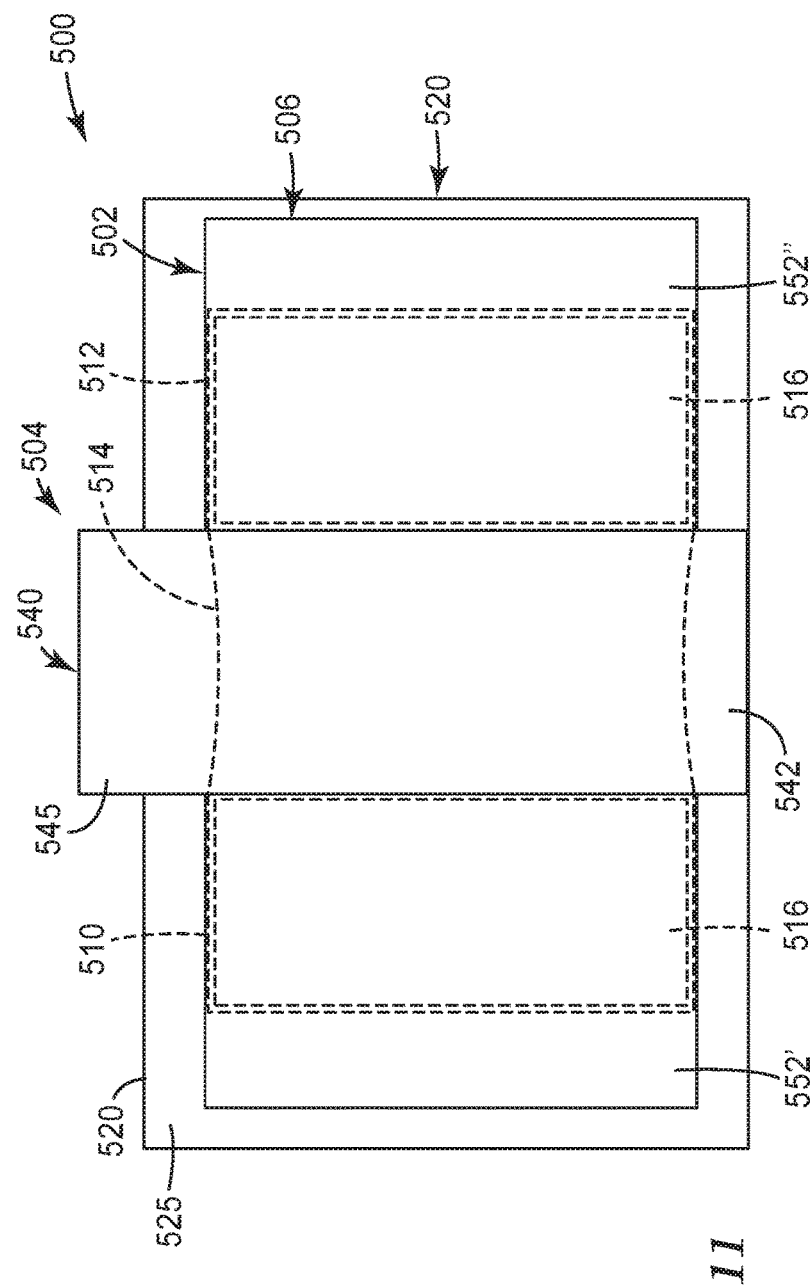
FIG. 11 is a schematic top plan view of the wound closure dressing system of FIG. 10.
Figure 12:
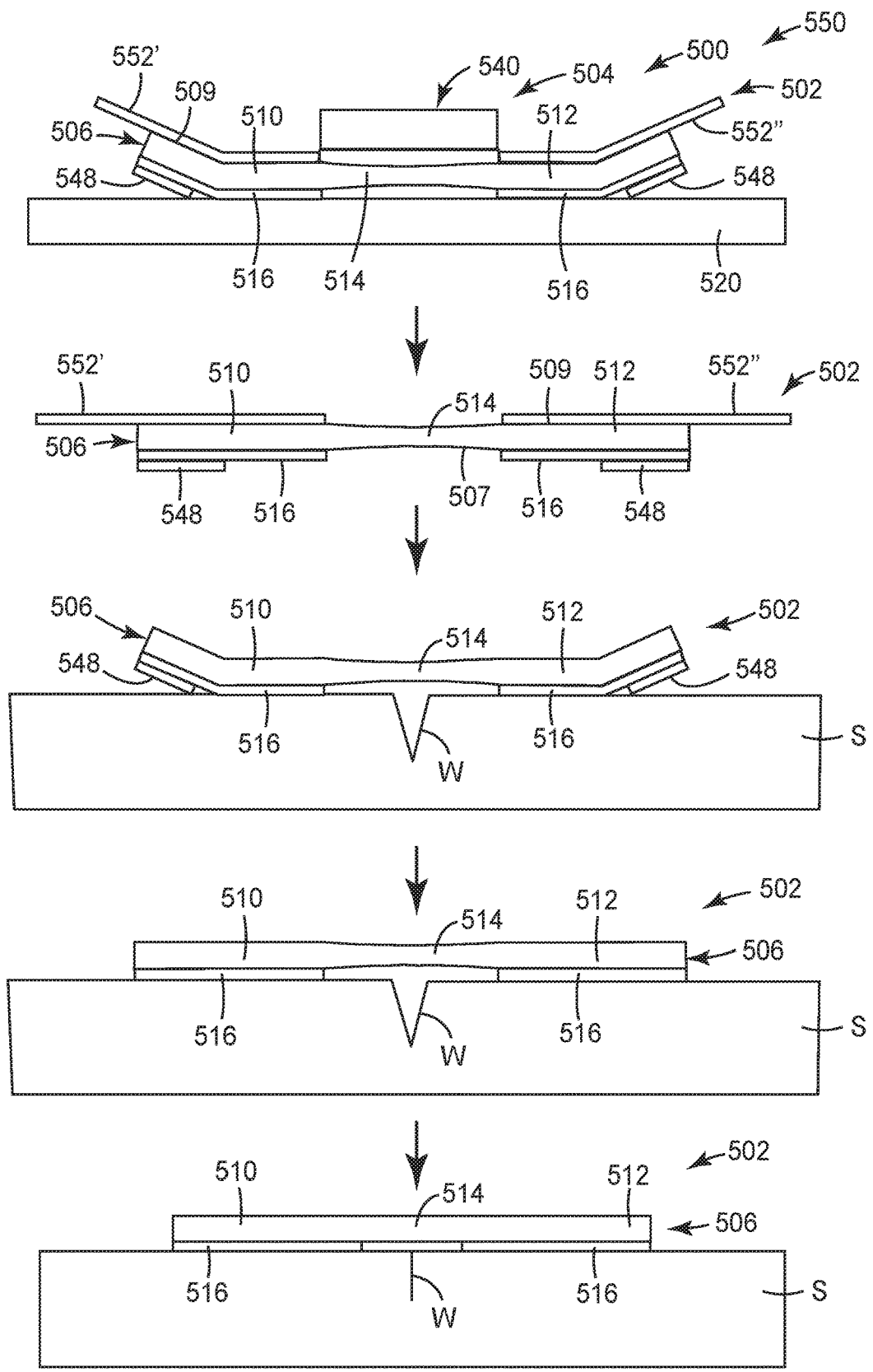
FIG. 12 illustrates a method of using the wound closure dressing system of FIGS. 10 and 11, shown in schematic side cross-sectional views, to apply the wound closure dressing to skin.

FIGS. 10-12 illustrate a wound closure dressing system 500 and wound closure dressing 502 according to another embodiment of the present disclosure. The wound closure dressing system 500 includes the wound closure dressing 502 and a support assembly 504. FIG. 12 further illustrates a method of using the wound closure dressing system 500 to apply the wound closure dressing 502 to skin.

The wound closure dressing 502 includes a viscoelastic backing 506 having a first major surface 507, a second major surface 509, a first end 510, a second end 512, and a middle section 514; and a skin-contact adhesive 516 on the first major surface 507 of the first end 510 and the second end 512 of the viscoelastic backing 506. By way of example, the viscoelastic backing 506 is illustrated in FIGS. 10-12 with the middle section 514 in a pre-stretched configuration.

As shown, the support assembly 504 includes a first support 520 configured to be coupled to the first major surface 507 of the viscoelastic backing 506, and a second support 540 configured to be coupled to the at least the second major surface 509 of at least the middle section 514 of the viscoelastic backing 506. The first support 520 and the second support 540 can also be configured to be coupled together. That is, in some embodiments, at least a portion of each of the first support 520 and the second support 540 extends beyond an edge or periphery of the wound closure dressing 502 (see FIG. 11), such that the first support 520 and the second support 540 can be coupled together. In some embodiments, the first support 520 and the second support 540 can be integrally formed (e.g., via a living hinge), and can instead be referred to as a first portion 520 and a second portion 540 of a support.

Similar to the support 120 of FIGS. 1-3, the first support 520 can have a first major surface 525 and a second major surface 527, and the wound closure dressing 502 can be adhered to the first major surface 525 of the support 520 via the skin-contact adhesive 516. As a result, any of the features described above with respect to the support 120 of FIGS. 1-3 can be applied to the first support 520 of FIGS. 10-12.

In addition, the second support 540 can be applied to the second major surface 509 of the backing 506, and particularly over any pre-stretched portion (e.g., the middle section 514, as shown), to further assist in maintaining the wound closure dressing 502 (i.e., the middle section 414 of the viscoelastic backing 506) in a pre-stretched configuration.

In some embodiments, the second support 540 can be formed of any of a variety of materials, including, but not limited to, the materials described above with respect to the support 120 of FIGS. 1-3, or the materials described above with respect to the overwrap 122 of FIGS. 1-3, other suitable materials, or a combination thereof.

In some embodiments, the first support 520 and the second support 540 can be formed of the same materials. However, in some embodiments, the first support 520 and the second support 540 can be formed of different materials. For example, in some embodiments, the first support 520 can be semi-rigid or rigid, and the second support 540 can be flexible, such that the first support 520 is more rigid than the second support 540. In some embodiments, as shown in FIGS. 10-11, the second support 540 can include a tape having a backing 542 and a pressure-sensitive adhesive 544 that can be configured to be adhered to the second major surface 509 of at least the middle section 514 of the backing 506 and further adhered to at least the first major surface 525 of the first support 520 (see FIG. 11). As such, the second major surface 509 (or a portion thereof) of the backing 506 can be configured to provide release characteristics to the pressure-sensitive adhesive 544 of the second support 540. The pressure-sensitive adhesive 544 can sometimes be referred to herein as a "support adhesive." Various adhesives can be employed as a support adhesive, as described in greater detail below in the 'Adhesives' section.

As further shown in FIG. 11, in some embodiments, the second support 540 can extend beyond an edge or periphery of the first support 520 to form a tab 545 that can facilitate removing the second support 540.

As shown in FIGS. 10 and 12, in some embodiments, the wound closure dressing 502 can further include a release liner 548 positioned to cover a portion (e.g., an outer portion) of the skin-contact adhesive 516 on at least one of the first end 510 and the second end 512, such that the portion of the skin-contact adhesive 516 that is covered by the release liner 548 is not adhered to the first support 520 and can form a tab to facilitate removal of the wound closure dressing 502 from the first support 520. Examples and features of release liners that can be employed are described in greater detail below.

As further shown in FIGS. 10-12, in some embodiments, the wound closure dressing 502 can include one or more carriers (or frames) 552, which can be more rigid than the viscoelastic backing 506 and can aid in application of the wound closure dressing 502, i.e., without wrinkling. Additional details regarding carriers that can be employed in wound closure dressings of the present disclosure are described in greater detail below.

By way of example, the wound closure dressing 502 includes a first carrier 552' coupled to the second major surface 509 of the first end 510 of the backing 506, and a second carrier 552" coupled to the second major surface 509 of the second end 512 of the backing 506. As shown, in some embodiments, one or both of the first carrier 552' and the second carrier 552" can extend beyond an edge or periphery of the backing 506 to form a tab that can be grasped to facilitate removal of the carriers 552' and 552", e.g., after the wound closure dressing 502 has been applied to skin. As shown in FIGS. 10 and 12, the second support 540 can be configured to be coupled to the second major surface 509 of the middle section 514 and located between the first carrier 552' and the second carrier 552".

A method of dressing or closing a wound will now be described with respect to FIG. 12, which illustrates a method 550 of using the wound closure dressing system 500 of FIGS. 10 and 11.

As shown in FIG. 12, the wound closure dressing system 500 can be provided with the wound closure dressing 502 coupled to the support assembly 504 in a pre-stretched configuration. Particularly, the middle section 514 of the viscoelastic backing 506 is provided in a pre-stretched configuration, and that pre-stretched configuration is maintained by the support assembly 504.

Then, the wound closure dressing 502 can be decoupled from the support assembly 504. Particularly, as shown in FIG. 12, the second support 540 can be removed from the wound closure dressing 502 and the first support 520 (e.g., by grasping the tab 545 (see FIG. 11) and peeling the second support 540 away from the second major surface 509 of the middle section 514). After the second support 540 is removed, there is a possibility that the viscoelastic backing 506 can begin to recover at least slightly from its pre-stretched configuration. However, after the second support 540 is removed, the wound closure dressing 502 still remains adhered to the first major surface 525 of the first support 520 via the skin-contact adhesive 516 (i.e., which adheres the portions of the first end 510 and the second end 512 of the backing 506 to the first support 520 that are not covered by the release liners 548). As a result, the adhesion between the skin-contact adhesive 516 and the first support 520 can be tuned to minimize recovery of the viscoelastic backing 506 while the viscoelastic backing 506 is still adhered to the first support 520.

As further shown in FIG. 12, the wound closure dressing 502 (which still includes the first and second carriers 552' and 552" and the release liners 548) can then be removed from the first support 520 by peeling the skin-contact adhesive 516 from the first major surface 525 of the first support 520 (see the second step shown in the method 550 of FIG. 12). The first end 510 and the second end 512 can be removed sequentially from the first support 520. Because of the viscoelastic properties of the viscoelastic backing 506, the viscoelastic backing 506 does not immediately recover from its pre-stretched elongation after the first support 520 is removed, and a user has time to properly apply the wound closure dressing 502.

The wound closure dressing 502 (i.e., the skin-contact adhesive 516 that is not covered by the release liners 548) can then be applied to skin S. Particularly, the first end 510 of the viscoelastic backing 506 can be applied to skin S adjacent a first side of a wound site W, and the second end 512 of the viscoelastic backing 506 can be applied to skin S adjacent a second side of the wound site W, opposite the first side, such that the middle section 514 is positioned over (i.e., in overlapping relationship with) the wound site W, but not adhered to the wound site W, as shown in the third step of FIG. 12. The first carrier 552' and the second carrier 552" can facilitate applying the more flexible (or flimsy) backing 506 without causing the backing 506 wrinkle upon application. After the wound closure dressing 502 has been applied to the skin S as desired, the first carrier 552' and the second carrier 552" can be removed from the second major surface 509 of the first end 510 and the second end 512 of the backing 506.

As shown in the fourth step of FIG. 12, the release liners 548 can then be removed from the outermost portions of the first end 510 and the second end 512 to fully adhere the skin-contact adhesive 516 of the first end 510 and the second end 512 of the backing 506 to the skin S.

The wound closure dressing 502, particularly, the viscoelastic backing 506, and more particularly, the pre-stretched middle section 514, can then be allowed to at least partially recover its deformation, while the wound closure dressing 502 remains adhered to the skin S, such that the wound closure dressing 502 exerts forces on the skin S to at least partially close the wound and/or to at least partially maintain the wound closed, as shown in the fifth step of FIG. 12.

Figure 13:
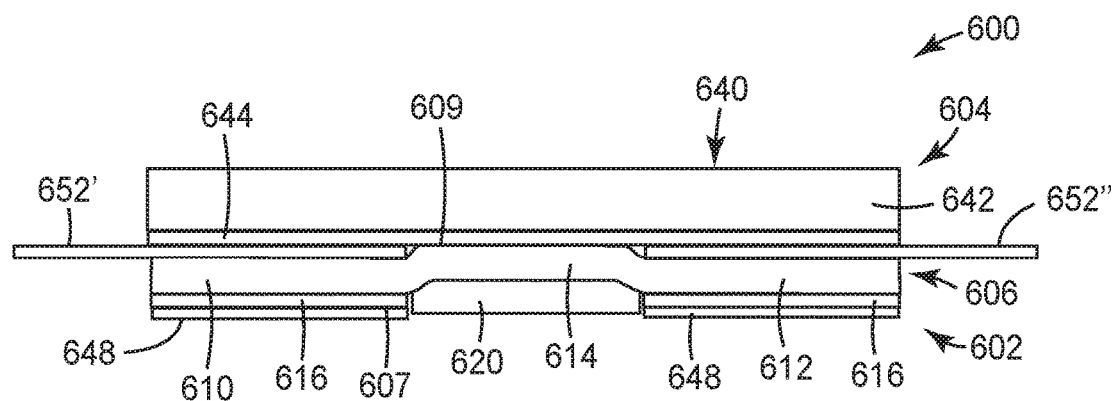
FIG. 13 is a schematic side cross-sectional view of a wound closure dressing system according to another embodiment of the present disclosure, the wound closure dressing system comprising a wound closure dressing.
Figure 14:
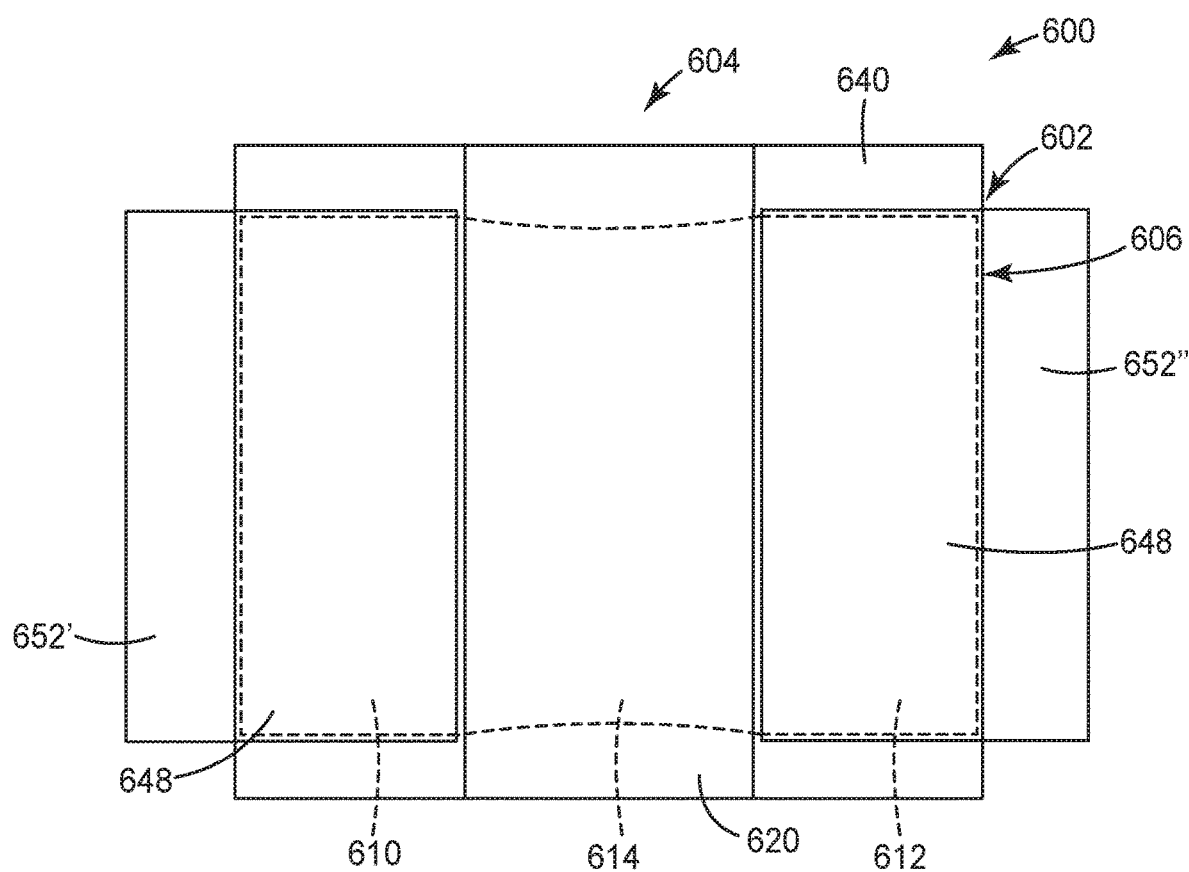
FIG. 14 is a schematic bottom plan view of the wound closure dressing system of FIG. 13.
Figure 15:
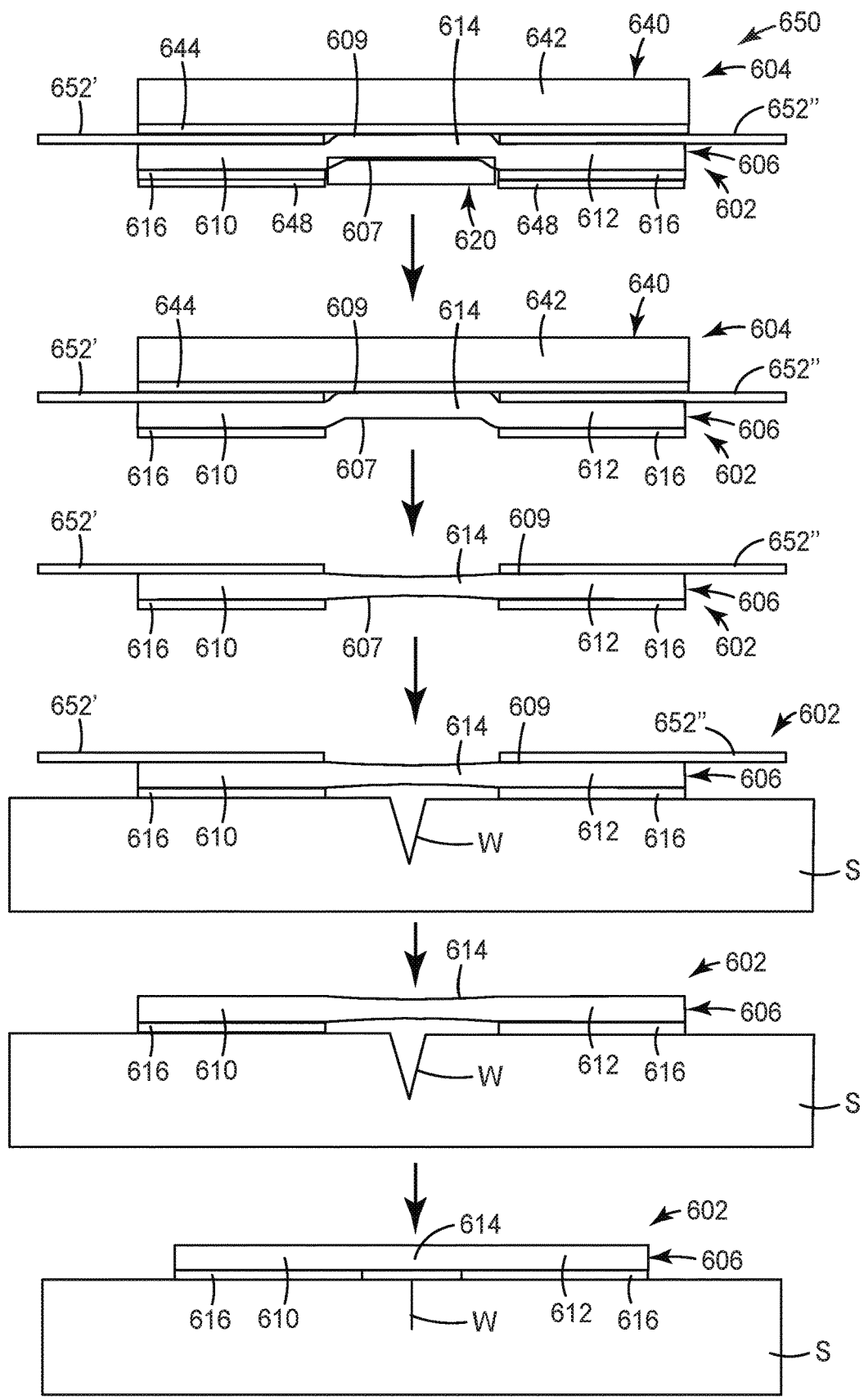
FIG. 15 illustrates a method of using the wound closure dressing system of FIGS. 13 and 14, shown in schematic side cross-sectional views, to apply the wound closure dressing to skin.

FIGS. 13-15 illustrate a wound closure dressing system 600 and wound closure dressing 602 according to another embodiment of the present disclosure. The wound closure dressing system 600 includes the wound closure dressing 602 and a support assembly 604. FIG. 14 is a bottom plan view of the wound closure dressing system 600, and FIG. 15 further illustrates a method of using the wound closure dressing system 600 to apply the wound closure dressing 602 to skin.

The wound closure dressing 602 includes a viscoelastic backing 606 having a first major surface 607, a second major surface 609, a first end 610, a second end 612, and a middle section 614; and a skin-contact adhesive 616 on the first major surface 607 of the first end 610 and the second end 612 of the viscoelastic backing 606. By way of example, the viscoelastic backing 606 is illustrated in FIGS. 13-15 with the middle section 614 in a pre-stretched configuration.

The wound closure dressing system 600 is similar to the wound closure dressing system 500 of FIGS. 10-12, wherein like numerals represent like elements. As such, reference is made to the description above accompanying FIGS. 10-12 for a more complete description of the features and elements (and alternatives to such features and elements) of the embodiments illustrated in FIGS. 8-15.

As shown, the support assembly 604 includes a first support 620 configured to be coupled to the first major surface 607 of the viscoelastic backing 606, and a second support 640 configured to be coupled to the at least second major surface 609 of at least the middle section 614 of the viscoelastic backing 606. In the embodiment of FIGS. 13-15, the second support 540 is coupled to the entire second major surface 609 of the backing 606, which can include or be at least partially defined by one or more carriers 652, as described below.

The first support 620 and the second support 640 can also be configured to be coupled together. That is, in some embodiments, at least a portion of each of the first support 620 and the second support 640 extends beyond an edge or periphery of the wound closure dressing 602 (see FIG. 14), such that the first support 620 and the second support 640 can be coupled together. In some embodiments, the first support 620 and the second support 640 can be integrally formed (e.g., via a living hinge), and can instead be referred to as a first portion 620 and a second portion 640 of a support.

Unlike the support 120 of FIGS. 1-3 and the first support 520 of FIGS. 10-12, the first support 620 is not coupled to the first and second ends 610 and 612 of the backing 606 via the skin-contact adhesive 616. Rather, the first support 620 can have a first major surface 625 and a second major surface 627 opposite the first major surface 625, and the first major surface 625 of the first support 620 can be coupled (e.g., adhered to or wrapped around) to the first major surface 607 of the middle section 614. As such, the first support 620 also does not provide release characteristics to the skin-contact adhesive 616, and the wound closure dressing 602 further includes release liners 648 positioned to cover the skin-contact adhesive 616 on the first end 610 and the second end 612 of the backing 606 until the wound closure dressing 602 is applied to skin.

The wound closure dressing 602 can further include a first carrier 652' and a second carrier 652", similar to the wound closure dressing 502 of FIGS. 10-12. As a result, as shown, in some embodiments, the second support 640 can be coupled (e.g., adhered) to the second major surface 609 of the middle section 614, the first carrier 652', and the second carrier 652". Furthermore, at least one of the first carrier 652' and the second carrier 652" can extend beyond an edge or periphery of the backing 606 to form a tab which can be grasped to facilitate decoupling the support assembly 604 from the wound closure dressing 602 and/or to facilitate applying the wound closure dressing 602 to skin.

In some embodiments, the first support 620 can be formed of any of the materials described above with respect to the support 120 of FIGS. 1-3, and can be coupled to the middle section 614 by a pressure-sensitive adhesive (not shown), which can sometimes be referred to herein as a "support adhesive." Various adhesives can be employed as a support adhesive, as described in greater detail below in the 'Adhesives' section. In other embodiments, the first support 620 can be formed of any of the materials described above with respect to the second support 540 of FIGS. 10-12 or the overwrap 122 of FIGS. 1-3. In some embodiments, the first support 620 can include a pressure-sensitive adhesive (i.e., a support adhesive) that can be configured to adhere to the first major surface 607 of the middle section 614 and the second support 640 (see FIG. 14).

In some embodiments, the second support 640 can include a backing 642 formed of any of the materials described above with respect to the support 120 of FIGS. 1-3 or any of the materials described above with respect to the second support 540 of FIGS. 10-12, and can further include a pressure-sensitive adhesive 644, which can sometimes be referred to herein as a "support adhesive." As such, the second major surface 609 (or a portion thereof) of the backing 606, as well as the first carrier 652' and the second carrier 652", can be configured to provide release characteristics to the pressure-sensitive adhesive 644 of the second support 640.

The combination of the first support 620 and the second support 640 can be used to effectively maintain the backing 606 (i.e., the middle section 614) in the pre-stretched configuration prior to use.

In some embodiments, the first support 620 and the second support 640 can be formed of the same materials. However, in some embodiments, the first support 620 and the second support 640 can be formed of different materials. For example, in some embodiments, the second support 620 can be semi-rigid or rigid, and the first support 620 can be flexible, such that the second support 640 is more rigid than the first support 620.

A method of dressing or closing a wound will now be described with respect to FIG. 15, which illustrates a method 650 of using the wound closure dressing system 600 of FIGS. 13 and 14.

As shown in FIG. 15, the wound closure dressing system 600 can be provided with the wound closure dressing 602 coupled to the support assembly 604 in a pre-stretched configuration. Particularly, the middle section 614 of the viscoelastic backing 606 is provided in a pre-stretched configuration, and that pre-stretched configuration is maintained by the support assembly 604.

Then, the wound closure dressing 602 can be decoupled from the support assembly 604. Particularly, as shown in the second step of FIG. 15, the first support 620 can be removed from the wound closure dressing 602 and the second support 640 by peeling the first support 620 away from the first major surface 607 of the middle section 614 and the second support 640 to expose the first major surface 607 of the middle section 614. After the first support 620 is removed, there is a possibility that the viscoelastic backing 606 can begin to recover at least slightly from its pre-stretched configuration. However, after the first support 620 is removed, the wound closure dressing 602 still remains adhered to the second support 640 via the support adhesive 644 (i.e., which adheres to the second major surface 609 of the middle section 614, the first carrier 652', and the second carrier 652").

As further shown in the second step of FIG. 15, the release liners 648 can also be removed to expose the skin-contact adhesive 616 on the first end 610 and the second end 612 of the backing 606 at this stage.

As shown in the third step of FIG. 15, the second support 640 can then be removed by peeling the backing 642 and the support adhesive 644 from the from the second major surface 609 of the middle section 614, the first carrier 652' and the second carrier 652". Because of the viscoelastic properties of the viscoelastic backing 606, the viscoelastic backing 606 does not immediately recover from its pre-stretched elongation after the second support 640 is removed, and a user has time to properly apply the wound closure dressing 602.

The wound closure dressing 602 can then be applied to skin S. Particularly, the first end 610 of the viscoelastic backing 606 can be applied to skin S adjacent a first side of a wound site W, and the second end 612 of the viscoelastic backing 606 can be applied to skin S adjacent a second side of the wound site W, opposite the first side, such that the middle section 614 is positioned over (i.e., in overlapping relationship with) the wound site W, but not adhered to the wound site W, as shown in the fourth step of FIG. 15.

The first carrier 652' and the second carrier 652" can facilitate applying the more flexible (or flimsy) backing 606 without causing the backing 606 to wrinkle upon application. After the wound closure dressing 602 has been applied to the skin S as desired, the first carrier 652' and the second carrier 652" can be removed from the second major surface 609 of the first end 610 and the second end 612 of the backing 606, as shown in the fifth step of FIG. 15.

The wound closure dressing 602, particularly, the viscoelastic backing 606, and more particularly, the pre-stretched middle section 614, can then be allowed to at least partially recover its deformation, while the wound closure dressing 602 remains adhered to the skin S, such that the wound closure dressing 602 exerts forces on the skin S to at least partially close the wound and/or to at least partially maintain the wound closed, as shown in the fifth and sixth steps of FIG. 15.

Carriers

The material used to form any carriers or carrier layers (which, in some embodiments, can include frames and/or tabs) employed in wound closure dressings of the present disclosure is generally substantially more rigid than the backings to prevent the backings from improperly wrinkling during application to a patient. The carriers, if employed, can be heat-sealable to the second major surface of the backing with or without a low adhesion backsize coating described above. In general, the carrier materials can include, but are not limited to, polyethylene/vinyl acetate copolymer-coated papers and polyester films. One example of a suitable material is a polyethylene/vinyl acetate copolymer coated super calendared Kraft paper (1-80BKG-157 PE; LOPAREX of Willowbrook, Ill.).

In some embodiments, the carriers can include perforations to aid in separating portions thereof after application of the wound closure dressing to a patient. Spacing and shape of the perforations are adjusted to provide a layer with relatively easy to tear performance on removal of the layer from the applied dressing. The perforations may be shaped in accordance with any of the accepted perforation patterns including linear, angled, Y-shaped, V-shaped, dual-angled offset, sinusoidal, etc.

Release Liners

Release liners suitable for use with the wound closure dressings of the present disclosure can include, but are not limited to, kraft papers, polyethylene, polypropylene, polyester, or combinations thereof. Such liners can be coated with release agents, such as fluorochemicals, silicones, or other suitable low surface energy materials. Other adhesives and release liner combinations known to those of ordinary skill in the art can also be employed in the wound closure dressings of the present disclosure. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films, commercially available from H. P. Smith Co., and fluoropolymer coated polyester films, commercially available from 3M Company (St. Paul) under the brand "SCOTCHPAK™" release liners.

Adhesives

As described above, in some embodiments, any support adhesive, if employed, can have an adhesion that is greater than the skin-contact adhesive. In some embodiments, the support adhesive and the skin-contact adhesive may be of the same or similar classes of adhesive, but have different adhesion levels. For example, the support adhesive and/or the skin-contact adhesive may be an acrylate, silicone, urethane, hydrogel, hydrocolloid, natural rubber, or synthetic rubber. Adhesion can also be tuned through changes in adhesive composition, adhesive thickness, or adhesive surface area (e.g., by employing a pattern-coated adhesive).

"Adhesion" refers to the force required to separate an adhesive from an underlying substrate. Adhesion can be measured in a number of ways. For example, adhesion can be defined by peel force or shear force. In some embodiments, adhesion can be defined by peel adhesion using ASTM D3330/D3330M-04(2010). In some embodiments, adhesion can be defined by shear adhesion using ASTM D3654M-06(2011). Adhesion is highly dependent on the specific substrate being adhered to, as well as the time the pressure-sensitive adhesive (PSA) is allowed to dwell on the substrate.

For example, typical peel adhesion values exhibited by pressure-sensitive adhesives in wound closure dressings maybe in the range of 20 to 300 g/cm as measured from stainless steel. In some embodiments, at least 10% higher peel adhesion, as measured by ASTM D3330/D3330M-04 (2010), of the support adhesive over the skin-contact adhesive may realize the benefit of both securing the support to the viscoelastic backing (and/or to another portion of the support), while providing gentle adhesion to the skin.

In some embodiments, the support adhesive can be an acrylate adhesive and the skin-contact adhesive can be a silicone adhesive or an acidic adhesive (e.g., acrylic acid-based). For example, in some embodiments, the support adhesive can be an isooctyl acrylate:acrylamide ("IOA-acrylamide") adhesive, and the skin-contact adhesive can be an isooctyl acrylate:acrylic acid ("IOA:AA") adhesive. In some embodiments, the support adhesive and the skin-contact adhesive can both include an IOA:AA adhesive. In some embodiments, any of the above adhesive combinations can be employed, but with 2-ethyl hexyl acrylate ("2-EHA") substituted for IOA.

The term "acrylate" or "acrylate-based" or "acrylate-containing" refers to monomeric acrylic or methacrylic esters of alcohols. Acrylate and methacrylate monomers are referred to collectively herein as "acrylate" monomers. Materials that are described as "acrylate-based" or "acrylate-containing" contain, or are derived from, at least some acrylate monomers and may contain additional co-monomers.

The term "acrylic acid" or "acrylic acid-based" or "acrylic acid-containing" refers to monomers comprising acrylic acid. Acrylic acid monomers are referred to collectively herein as "acrylic acid" monomers. Materials that are described as "acrylic acid-based" or "acrylic acid-containing" contain, or are derived from, at least some acrylic acid monomers and may contain additional co-monomers. This class of adhesives also falls within the broader class of acidic adhesives (i.e., adhesives comprising an acidic component), and in some embodiments, the skin-contact adhesive can include an acidic adhesive, and particularly, an acrylic acid-based adhesive.

Suitable acrylate adhesives that can be applied to skin such as the acrylate copolymers are described in U.S. Pat. No. RE 24,906, the disclosure of which is hereby incorporated by reference. In particular, a 97:3 iso-octyl acrylate:acrylamide copolymer. Another acrylate adhesive is an 70:15:15 isooctyl acrylate: ethyleneoxide acrylate:acrylic acid terpolymer, as described in U.S. Pat. No. 4,737,410 (Example 31), the disclosure of which is hereby incorporated by reference. Other useful acrylate adhesives are described in U.S. Pat. Nos. 3,389,827, 4,112,213, 4,310,509, and 4,323,557, the disclosures of which are incorporated herein by reference.

The term "silicone" or "silicone-based" or "silicone-containing" refers to polymers that contain units with dialkyl or diaryl siloxane (—SiR$_2$O—) repeating units. The silicone-based polymers may be segmented copolymers or polysiloxanes polymers. The terms silicone and siloxane are used interchangeably.

Generally, silicone adhesives are able to effectively secure materials or substrates to skin and upon removal from the skin produce little or no skin damage. In some embodiments, one or both of the support adhesive and the skin-contact adhesive can include a silicone adhesive.

Examples of suitable silicone adhesive systems can include, but are not limited to, products available under the following trade designations: Dow Corning MG 7-9850, Wacker SILPURAN® 2110 and 2130, Bluestar SILBIONE® RT Gel 4317 and 4320, Nusil MED-6345 and 6350. Other examples of suitable silicone adhesives are disclosed in PCT Publications WO2010/056541, WO2010/056543 and WO2010/056544, the disclosures of which are incorporated herein by reference.

For skin-contact adhesives, it is desirable that the adhesive is able to transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as perforating the adhesive or pattern coating the adhesive, as described in U.S. Pat. No. 4,595,001 and U.S. Pat. App. Pub. 2008-0233348, the disclosures of which are incorporated herein by reference. As mentioned above, in some embodiments, each of the support and skin-contact adhesives can optionally be applied in a patterned or discontinuous manner.

In some embodiments, the skin-contact adhesive can have an average peel strength on stainless steel, e.g., when tested according to the 180° Peel Test Method described in the Examples below, that is at least 2 N/cm; in some embodiments, at least 2.2 N/cm; in some embodiments, at least 2.4 N/cm; and in some embodiments, at least 2.8 N/cm. In some embodiments, the skin-contact adhesive can have an average peel strength on stainless steel that is no greater than 6 N/cm; in some embodiments, no greater than 5 N/cm; and in some embodiments, no greater than 4 N/cm.

Absorbent Layers

Absorbent layers of the present disclosure can include a foam or gel. Examples of suitable foams are described, e.g., in U.S. Pat. Nos. 6,881,875 and 6,977,323, each of which is incorporated by reference herein. Examples of suitable gels (e.g., hydrogels) are described in U.S. Publication No. 2009/0187130, and U.S. Pat. No. 7,005,143, each of which is incorporated herein by reference.

The absorbent layer can include any material that is conformable, non-irritating to the wearer's skin, and capable of absorbing and retaining liquids. The absorbent layer may be a single layer or multilayer material, where if it is a multilayer material, each layer may be of the same material or of different materials.

Examples of materials that would be suitable for the absorbent layer include creped cellulose wadding; melt blown polymers; chemically stiffened, modified or cross-linked cellulosic fibers; tissue; absorbent foams; absorbent sponges; superabsorbent polymers; absorbent gelling materials; or any other known absorbent material or combinations of materials. The absorbent layer may further comprise minor amounts (typically less than 10%) of non-liquid absorbent materials, such as adhesives, waxes, oils, antimicrobials, active ointments, and the like, for example.

In some embodiments, the absorbent layer can be an open-cell foam. The foam may include a synthetic polymer that is adapted to form a conformable open-cell foam that absorbs the wound exudate. In some embodiments, open cell cellulose-based foams can be employed. Examples of suitable materials for the foams include synthetic organic polymers including, but not limited to: polyurethanes, carboxylated butadiene-styrene rubbers, polyesters, polyacrylates, or combinations thereof. In some embodiments, the polymeric foams can be made of one or more types of monomers (e.g., copolymers) or mixtures (e.g., blends) of polymers. Examples of foam materials are described in the book entitled *Flexible Polyurethane Foams*, Dow Polyurethanes, editors R. Herrington and K. Hock, 1997.

The foams can be of a wide range of thicknesses; from about 0.5 mm or 1 mm to about 30 mm or 80 mm thick. Furthermore, they can include one or more layers tailored to have the desired properties. These layers can be directly bonded to each other or bonded together with adhesive layers. Optionally, disposed between these layers can be one or more layers of polymeric netting or nonwoven, woven, or knit webs for enhancing the physical integrity of the foam. In some embodiments, the second surface of the absorbent layer can include a foam with a skin to prevent fluid passage through the absorbent layer.

In some embodiments, the absorbent layer can include superabsorbing particles or fibers contained within a porous pouch. Examples include superabsorbent fibrous webs that are available from National Nonwovens, Cincinnati, Ohio, or sachets containing superabsorbent material such as Sorbion Sachet S available from Sorbion AG, Senden, Germany.

In some embodiments, the absorbent body can include a wound-contacting layer bonded to the skin-facing surface of the absorbent layer. Examples of such wound-contacting layers include polymeric netting and porous (e.g., perforated) films, or other conventional materials that prevent the dressing from sticking to the wound. Such a wound-contacting layer can be bonded directly to the absorbent layer (e.g., cast or thermomechanical bonding), or bonded to the absorbent layer using an adhesive layer, for example.

One example of a suitable absorbent layer is found in a 3M™ TEGADERM™ High Performance Foam Dressing available from 3M Company of St. Paul, Minn. Suitable constructions for the absorbent layer are disclosed in U.S. Pat. Nos. 6,838,589; 7,030,288; and 7,612,248, the disclosures of which are herein incorporated by reference.

In some embodiments the absorbent layer can include a relatively low-adhesion (i.e., compared to the skin-contact adhesive) adhesive. For example, in some embodiments, the absorbent layer can include an adhesive having an average peel strength on stainless steel, e.g., when tested according to the 180° Peel Test Method described in the Examples below, that is less than 2 N/cm; in some embodiments, less than 1.8 N/cm, and in some embodiments, less than 1.7 N/cm. In some embodiments, the absorbent layer can include an adhesive having an average peel strength on stainless steel that is at least 0.2 N/cm; in some embodiments, at least 0.4 N/cm; and in some embodiments, at least 0.6 N/cm.

In some embodiments, the absorbent layer can include an adhesive having an average peel strength on a given substrate, e.g., when tested according to the 180° Peel Test Method described in the Examples below, that is at least 0.5 N/cm less than the average peel strength of the skin-contact adhesive on the same substrate; in some embodiments, at least 0.7 N/cm less; in some embodiments, at least 0.8 N/cm less; in some embodiments, at least 0.9 N/cm less; in some embodiments, at least 1.0 N/cm less; in some embodiments, at least 1.1 N/cm less; and in some embodiments, at least 1.2 N/cm less.

In some embodiments the absorbent layer can include a silicone material (e.g., gel) that is configured for wound contact. While the silicone wound contact material may only minimally absorb wound exudate, it can still provide benefits from sealing the surface of the wound or minimizing scarring. In some embodiments, such a silicone material can include silicones produced through hydrosilation, peroxide-activated cure, dehydrogenative coupling, condensation, or moisture cure, other suitable mechanisms, or combinations thereof. In some embodiments, the silicone material can be made with electron beam or gamma ray curing of low molecular weight silicones, including non-functional silicones. In some embodiments, the silicone material can include silicone copolymers including silicone polyoxamide copolymers, silicone polyoxamide-hydrazide copolymers, other suitable silicone copolymers, or combinations thereof.

Each embodiment shown in the figures is illustrated as a separate embodiment for clarity in illustrating a variety of features of the wound closure dressings and wound closure dressing systems of the present disclosure. However, it should be understood that any combination of elements and features of any of the embodiments illustrated in the figures and described herein can be employed in the wound closure dressings and wound closure dressing systems of the present disclosure.

The following embodiments are intended to be illustrative of the present disclosure and not limiting.

EMBODIMENTS

1. A wound closure dressing comprising:
a viscoelastic backing comprising a first major surface configured to face skin when in use, a first end, a second end, and a middle section located between the first end and the second end, wherein the viscoelastic backing recovers, at room temperature:
no more than 40% of its deformation after 10 seconds, after being strained to 50% elongation for 30 minutes, and
at least 70% of its deformation after 48 hours, after being strained to 50% elongation for 30 minutes;
a skin-contact adhesive on the first major surface of the viscoelastic backing adjacent the first end and the second end, a majority of the first major surface of the middle section being free of the skin-contact adhesive.

2. The wound closure dressing of embodiment 1, wherein the viscoelastic backing recovers, at room temperature:
no more than 30% of its deformation after 10 seconds, after being strained to 50% elongation for 30 minutes.

3. The wound closure dressing of embodiment 1 or 2, wherein the viscoelastic backing recovers, at room temperature:
at least 90% of its deformation after 48 hours, after being strained to 50% elongation for 30 minutes.

4. The wound closure dressing of any of embodiments 1-3, wherein the viscoelastic backing is in a pre-stretched configuration.

5. The wound closure dressing of any of embodiments 1-4, wherein only the middle section of the viscoelastic backing is in the pre-stretched configuration.

6. The wound closure dressing of any of embodiments 1-5, wherein the middle section of the viscoelastic backing is in a pre-stretched configuration.

7. The wound closure dressing of any of embodiments 1-6, wherein:
the first end is configured to be secured to skin on one side of a wound site;
the second end is configured to be secured to skin on an opposite side of the wound site from the first end; and
the middle section is configured to be positioned over the wound site.

8. The wound closure dressing of any of embodiments 1-7, wherein the viscoelastic backing further includes a second major surface opposite the first major surface, and wherein the wound closure dressing further includes a carrier coupled to the second major surface.

9. The wound closure dressing of embodiment 8, wherein at least a portion of the carrier is positioned to extend beyond an edge of the viscoelastic backing to form a tab.

10. The wound closure dressing of any of embodiments 1-9, wherein the skin-contact adhesive is patterned on the first major surface of the middle section.

11. The wound closure dressing of any of embodiments 1-10, further comprising an absorbent layer coupled to the first major surface of the middle section of the viscoelastic backing.

12. The wound closure dressing of embodiment 11, wherein the absorbent layer is transparent.

13. The wound closure dressing of embodiment 11 or 12, wherein the absorbent layer includes a hydrogel.

14. The wound closure dressing of any of embodiments 11-13, wherein the absorbent layer includes a foam.

15. The wound closure dressing of any of embodiments 11-14, wherein the absorbent layer is positioned adjacent a lateral side of the middle section of the viscoelastic backing.

16. A wound closure dressing kit comprising:
a first wound closure dressing according to the wound closure dressing of any of embodiments 1-15, wherein the viscoelastic backing of the first wound closure dressing is pre-stretched by a first percent elongation; and
a second wound closure dressing according to the wound closure dressing of any of embodiments 1-15, wherein the viscoelastic backing of the second wound closure dressing is pre-stretched by a second percent elongation that is less than the first percent elongation.

17. A wound closure dressing system comprising:
the wound closure dressing of any of embodiments 1-15, with the viscoelastic backing in a pre-stretched configuration; and
a support assembly;
wherein the wound closure dressing is coupled to the support with the viscoelastic backing in the pre-stretched configuration, such that the pre-stretched configuration of the viscoelastic backing is maintained until the wound closure dressing is decoupled from the support.

18. The system of embodiment 17, wherein the support assembly includes a support that is rigid relative to the viscoelastic backing.

19. The system of embodiment 17 or 18, wherein the support assembly includes a support, and wherein the wound closure dressing is coupled to the support via the skin-contact adhesive.

20. The system of embodiment 19, wherein the support provides release characteristics to the skin-contact adhesive, while also providing sufficient adhesion to maintain the viscoelastic backing in its pre-stretched configuration.

21. The system of embodiment 19 or 20, further comprising a release liner positioned to cover a portion of the skin-contact adhesive, such that the portion of the skin-contact adhesive covered by the release liner is not adhered to the support.

22. The system of any of embodiments 19-21, wherein the wound closure dressing is further coupled to the support via an overwrap that is positioned around at least a portion of the wound closure dressing and the support.

23. The system of any of embodiments 19-22, wherein the wound closure dressing is further coupled to the support via a fastener.

24. The system of any of embodiments 19-23, wherein the wound closure dressing is further coupled to the support via a first fastener positioned to couple the first end of the viscoelastic backing to the support and a second fastener positioned to couple the second end of the viscoelastic backing to the support.

25. The system of embodiment 24, wherein the first end and the second end each further include a perforated line located internally relative to the first fastener and the second fastener.

26. The system of embodiment 17, wherein the support assembly includes
a first support configured to be coupled to the first major surface of the viscoelastic backing, and
a second support configured to be coupled to a second major surface opposite the first major surface of at least the middle section of the viscoelastic backing.

27. The system of embodiment 26, wherein the first support and the second support of the support assembly are further configured to be coupled together.

28. The system of embodiment 26 or 27, wherein the first support and the second support each extend beyond an edge of the wound closure dressing, such that the first support and the second support can be coupled together.

29. The system of any of embodiments 26-28, wherein the second support extends beyond an edge of the first support to form a tab.

30. The system of any of embodiments 26-29, wherein the second support is coupled to the second major surface of the viscoelastic backing via a pressure-sensitive adhesive.

31. The system of any of embodiments 26-30, wherein the first support is coupled to the first major surface of at least the middle section of the viscoelastic backing.

32. The system of embodiment 31, further comprising a release liner coupled to the skin-contact adhesive on the first end and the second end of the viscoelastic backing.

33. The system of embodiment 31 or 32, wherein the wound closure dressing further includes a first carrier coupled to the second major surface of the first end of the viscoelastic backing and a second carrier coupled to the second end of the viscoelastic backing.

34. The system of embodiment 33, wherein the second support is coupled to the second major surface of the middle section, the first carrier, and the second carrier.

35. The system of embodiment 33 or 34, wherein the second support is coupled to the second major surface of the middle section, the first carrier, and the second carrier via a pressure-sensitive adhesive.

36. The system of any of embodiments 33-35, wherein at least one of the first carrier and the second carrier extends beyond an edge of the viscoelastic backing to form a tab.

37. The system of any of embodiments 33-36, wherein the first carrier and the second carrier extend beyond an edge of at least one of the first support and the second support.

38. A method of dressing a wound, the method comprising:
providing the wound closure dressing system of any of the embodiments of 17-37;
decoupling the wound closure dressing and the support assembly; and
applying the wound closure dressing to skin after removing the wound closure dressing from the support.

39. The method of embodiment 38, further comprising allowing the pre-stretched viscoelastic backing to recover.

40. The method of embodiment 38 or 39, wherein applying the wound closure dressing to skin includes applying a first end of the viscoelastic backing to one side of a wound site and applying a second end of the viscoelastic backing to an opposite side of the wound site from the first end, such that the middle section is positioned over the wound site.

41. The method of any of embodiments 38-40, wherein decoupling the wound closure dressing and the support assembly includes decoupling a first support from at least a portion of the first major surface of the viscoelastic backing and decoupling a second support from at least a portion of the second major surface of the viscoelastic backing.

42. The method of embodiment 41, wherein decoupling the first support occurs prior to decoupling the second support.

43. The method of embodiment 41 or 42, wherein decoupling the second support occurs prior to decoupling the first support.

44. The method of any of embodiments 38-43, further comprising removing an overwrap from the wound closure dressing system prior to decoupling the wound closure dressing system and the support.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The following working examples are intended to be illustrative of the present disclosure and not limiting.

EXAMPLES

Materials
Materials utilized in the Examples are shown in Table 1.

TABLE 1

Materials List

| Material | Description | Source |
|---|---|---|
| Fomrez 44-111 | Poly(butylene adipate) Polyol | Chemtura Corporation, Middlebury, CT |
| 1,4-Butanediol | 1,4-Butanediol | Ashland, Inc, Covington, KY |
| Glycerol | Ultrapure HPLC grade, #38988 | Alfa Aesar, Ward Hill, MA |
| DBTDL | Di-n-butyltin dilaurate, 95%, #71130 | Alfa Aesar, Ward Hill, MA |
| Desmodur-W | Bis(4-isocyanatocyclohexyl) methane | Bayer Material Science, Pittsburgh, PA |
| K-Kat XK-651 | Bismuth catalyst in paraffinic distillates | King Industries, Inc. Norwalk, CT |
| Bicat 8 | Bismuth and Zinc Carboxylate Mixture | Shepherd Chemical Company, Norwood, OH |
| Polypropylene Sheet | 0.031" Polypropylene homopolymer | KMac Plastics, Grand Rapids, MI |
| Polyester Tape | Polyester Silicone Adhesive Tape 8403 | 3M, St. Paul, MN |
| Acrylic Adhesive | Pressure sensitive adhesive used on 3M Tegaderm Film Dressing, 1624W | 3M, St. Paul, MN |
| Release liner | Release liner used on 3M Tegaderm Film Dressing, 1624W | 3M, St. Paul, MN |
| Antibacterial Gel Pad | Gel pad from Tegaderm™ CHG IV Securement Dressing 1658 | 3M, St. Paul, MN |

Test Methods
Backing Recovery

Pieces of backing were cut to 7 cm long and 12.7 mm wide. A piece of polyester tape was wrapped around each end to produce two 2.5 cm×2.5 cm tabs, separated by 6 cm. Ink marks were placed at each end of the 6 cm gauge length. The tabs on each end of the strand were loaded into grips of a tensile load frame (Model 3365, Instron, Norwood, Mass.) equipped with 100 N capacity load cell. The initial grip separation was 6 cm and the temperature was 23° C. The grips were then separated at a rate of 30 cm/min to a displacement of 3 cm (i.e. a grip separation of 9 cm) and held at that displacement for 30 minutes. The backing sample was then removed and left in an unconstrained state to monitor elastic recovery. The distance between the ink marks was measured 10 seconds after removal from the grips and 48 hours after removal from the grips. The percentage of elongation that was recovered was calculated by taking the difference between the final grip separation and the distance between ink marks and dividing that value by the initial change in length (i.e. 3 cm). Three replicate tests were done for each sample, and the average values are reported.

Recovery on Skin

The wound closure dressing system was allowed to rest at room temperature for at least 24 hours after assembly, and during this time, the middle section was confirmed to have retained its initial degree of elongation. The wound closure dressing was removed from its support assembly and applied to skin with no added tension. The width of the middle section was measured immediately after application, 4 minutes after application and 20 minutes after application. The recovery of the middle section was calculated by taking the difference between the maximum middle section width (i.e. the width when on the support assembly) and the instant middle section width and dividing that value by the difference between the maximum middle section width and the initial middle section width before stretching.

180° Peel Test Method

Test materials were laminated to Viscoelastic Backing 2 and cut to strips with a width of 1.3 cm. The force required to peel the test material from a substrate at an angle of 180 degrees was measured using a peel force tester, model 3M90, obtained from Instrumentors, Inc., Strongsville, Ohio. The free end of a sample was doubled back nearly touching itself so the angle of removal was 180°. The free end was attached to the adhesion tester scale. The platen was then moved away from the scale at a speed of 12 in./min (0.305 m/min.), and the adhesive peel force was averaged for 5 seconds. At least three 6-second averages were measured, and those results were then averaged to produce the reported value.

Skin Irritation

Wound closure dressings were applied to healthy skin of hairless guinea pigs. The tests were done without a wound under the dressings, so the test is a simulation of a wound closure application. The effects of each type of dressing on the skin were observed, and irritation of the skin was particularly considered.

Wound closure dressings were removed from their support assemblies and immediately applied to one side of the back of a hairless guinea pig with no manually applied tension. A second replicate animal was tested with the same protocol. The dressings were covered with a foam-based covering to protect the test sites.

After 24 hours, the dressings were observed. The dressings were removed from the skin, and the skin under the applied dressings was then observed.

EXAMPLES

Viscoelastic Backing 1

A polyurethane film was prepared by reactive extrusion. The film was formed from a mixture of Fomrez 44-111 (44.4 wt %), 1,4-butanediol (10.4 wt %), glycerol (0.2%), DBTDL (0.08%), and Desmodur-W (45 wt %) and was 0.13 mm thick.

Viscoelastic Backing 2

A polyurethane film was prepared by reactive extrusion. The film was formed from a mixture of Fomrez 44-111 (45.2 wt %), 1,4-butanediol (10.1 wt %), glycerol (0.5%), K-Kat XK-651 (0.2%), and Desmodur-W (43.9 wt %) and was 0.05 mm thick.

Viscoelastic Backing 3

A polyurethane film was prepared by reactive extrusion. The film was formed from a mixture of Fomrez 44-111 (45.2 wt %), 1,4-butanediol (10.4 wt %), glycerol (0.3%), Bicat 8 (0.1%), and Desmodur-W (43.9 wt %) and was 0.04 mm thick.

Example-1—Wound Closure Dressing System Comprising Viscoelastic Backing 1

Two strips of acrylic adhesive, 1.9 cm wide by 12.7 cm long by 0.003 cm thick, were laminated to one surface of Viscoelastic Backing 1. The strips were parallel and placed 1.27 cm apart. A 5 cm by 5 cm piece of laminate was cut. The laminate formed the wound closure dressing of this example. Black ink was used to mark the inside edge of the adhesive tape on the viscoelastic backing. One of the adhesive strips was then laminated to a polypropylene sheet such that the outside edge of the tape was aligned with one outside edge of the polypropylene sheet. This end was then clamped. The polypropylene sheet served as a support for the system. The opposing, second end of the backing was then grasped and a middle section of the backing was heated with a heat gun for several seconds. When the middle section of the backing became more compliant, the backing was stretched such that the ink lines were approximately 2.5 cm apart (approximately 100% elongation of the middle section). The second end was then adhered to the polypropylene sheet. Two strips of polyester tape (2.5 cm×13 cm) were wrapped over the assembly in the same direction as the direction of stretching (i.e., along the strain axis) to each form a complete wrap around both faces of the assembly and such that the side edges of the strips overlapped each other by approximately 2 cm. The strips of polyester tape provided a first portion of a support for the system, and the polypropylene sheet provided a second portion of the support.

Example 2—Wound Closure Dressing System Comprising Viscoelastic Backing 3 and Liner Tab Two strips of acrylic adhesive 1.9 cm wide by 8.0 cm long by 0.003 cm thick were laminated to one surface of Viscoelastic Backing 3. The strips were parallel and placed 1.5 cm apart. A 5 cm by 8 cm piece of laminate was cut. The laminate formed the wound closure dressing of this example. The surface of the Viscoelastic Backing 3 was stamped with an ink grid with a 0.5 cm spacing between lines to help observe stretch and recovery of the backing. One of the adhesive strips was then laminated to a polypropylene sheet such that the outside edge of the tape was aligned with one outside edge of the polypropylene sheet. This end was then clamped. The polypropylene sheet served as a support for the system. A strip of release liner 9 mm wide was placed on the outer edge of the opposing, second end of the laminate, covering an outer portion (i.e., the outer 9 mm) of the adhesive, to produce a finger tab. This end was then grasped and a middle section of the backing was heated with a heat gun for several seconds. When the middle section of the backing became more compliant, the backing was stretched such that the middle section between the adhesive strips was approximately 3.0 cm wide (approximately 100% elongation of the middle section). The second end was then adhered to the polypropylene sheet. The liner provided a finger tab for easy removal from the polypropylene sheet. Two strips of polyester tape (5 cm×25 cm) were wrapped over the assembly in the same direction as the direction of stretching (i.e., along the strain axis) to each form a complete wrap around both faces of the assembly and such that the side edges of the strips overlapped each other by approximately 2 cm. The strips of polyester tape provided a first portion of a support for the system, and the polypropylene sheet provided a second portion of the support.

Example 3—Wound Closure Dressing System Comprising Viscoelastic Backing 3 and Liner Tab This example was prepared as described in Example 2, except the middle section was stretched from its initial width of 1.5 cm to approximately 2.3 cm (approximately 50% elongation of the middle section).

Example 4—Wound Closure Dressing System Comprising Viscoelastic Backing 3 and Antibacterial Gel Pad Two strips of acrylic adhesive 1.9 cm wide by 8.0 cm long by 0.003 cm thick were laminated to one surface of Viscoelastic Backing 3. The strips were parallel and placed 1.5 cm apart. A 6 cm by 8 cm piece of laminate was cut. The surface of the Viscoelastic Backing 3 was stamped with an ink grid with a 0.5 cm spacing between lines to help observe stretch and recovery of the backing. A strip of Antibacterial Gel Pad, 1.5 cm by 8.0 cm by 0.03 cm, was laminated to a first major surface of the backing in the area between the two adhesive strips (i.e., in the middle section of the backing). The laminate including the gel pad formed the wound closure dressing of this example. One of the adhesive strips was then laminated to a polypropylene sheet such that the outside edge of the tape was aligned with one outside edge of the polypropylene sheet. This end was then clamped. The polypropylene sheet served as a support for the system. The opposing, second end was then grasped and a middle section of the backing was heated with a heat gun for several seconds. When the middle section of the backing became more compliant, the backing was stretched such that the middle section between the adhesive strips was approximately 3.0 cm wide (i.e., the middle section was strained to 100% elongation). The second end was then adhered to the polypropylene sheet. Two strips of polyester tape (5 cm×25 cm) were wrapped over the assembly in the same direction as the direction of stretching (i.e., along the strain axis) to each form a complete wrap around both faces of the assembly and such that the side edges of the strips overlapped each other by approximately 2 cm. The strips of polyester tape provided a first portion of a support for the system, and the polypropylene sheet provided a second portion of the support.

Example 5—Wound Closure Dressing System Comprising Viscoelastic Backing 2 and Carrier A piece of polypropylene sheet was cut to 80 mm×75 mm. One face of this sheet was wiped with tape primer 94, and this face was then laminated to a piece of acrylic transfer tape 9471LE. Two strips of EVA-coated paper 3.4 cm by 21 cm were laminated to a piece of Viscoelastic Backing 2 that was 6 cm×30 cm at 90° C. The strips were parallel and placed 1.5 cm apart with equal portions of the paper overhanging each edge of the backing. These strips will form a carrier of the dressing, which can be used during application, i.e., when the dressing is removed from the polypropylene sheet. Two strips of acrylic adhesive 2.3 cm wide by 8.0 cm long by 0.003 cm thick were laminated to the surface of the backing opposite to the EVA-coated paper. The strips were parallel and placed 1.5 cm apart. The laminate was cut to a backing width of 8 cm (i.e., to a backing size of 6 cm×8 cm). The laminate formed the wound closure dressing of this example. The surface of the Viscoelastic Backing 2 between the EVA-coated paper strips was stamped with an ink grid with a 0.5 cm spacing between lines to help observe stretch and recovery of the backing. One of the EVA-coated paper strips was then laminated to the adhesive coated polypropylene sheet such that the outside edge of the backing was aligned with one outside edge of the polypropylene sheet. This end was then clamped. The opposing, second end was then grasped and the middle section of the backing was heated with a heat gun for several seconds. When the middle section of the backing became more compliant, the backing was stretched such that the middle section between the adhesive strips was approximately 3.0 cm wide. The second end was then adhered to the polypropylene sheet. One strip of polyester tape 3 cm by 8 cm was laminated over the stretched center section of the backing to keep the assembly adhered to the polypropylene sheet, while maintaining the middle section in a stretched configuration. This example is shown in FIGS. 13-15. The strip of polyester tape served as a first portion of a support for the system, and the polypropylene sheet served as a second portion of the support.

Example 6—Wound Closure Dressing System Comprising Partially-Stretched Viscoelastic Backing 2

Two strips of acrylic adhesive, 1.75 cm wide by 20 cm long and 0.0025 inches thick, were laminated to one surface of a piece of Viscoelastic Backing 2 (20 cm×10 cm), such that the strips were parallel and separated by 0.5 cm, each adhesive strip being covered by a release liner. Pieces were cut from this laminate that were 3.5 cm wide. The excess viscoelastic backing without adhesive coating on each edge was trimmed off to create a wound closure dressing that was 3.5 cm wide and 4 cm long. Post-It paper (3.5 cm×1.75 cm) was placed over each adhesive strip on the face of the viscoelastic backing opposite the adhesives. One of the adhesive strips was then laminated to a polypropylene sheet (5 cm×10 cm) such that the outside edge of the tape was aligned with one outside edge of the polypropylene sheet. This end was then clamped. The polypropylene sheet served as a support for the system. Part of the release liner was then peeled back from the other adhesive strip. That end of the dressing was stretched by hand (no heat) until the middle section (i.e., the area between the adhesive strips) had lengthened from 0.5 cm to 1 cm. The other adhesive strip was then adhered to the polypropylene sheet. The Post-It paper was removed to leave a dressing 4.5 cm long and 3.5 cm wide with a stretch ratio of 100% only in the middle section of the dressing. A strip of polyester tape (5 cm wide) was then wrapped around both faces of the assembly in the same direction as the direction of stretching (i.e., along the strain axis) to form a complete wrap around both faces of the assembly. The strip of polyester tape provided a first portion of a support for the system, and the polypropylene sheet provided a second portion of the support.

Comparative Examples CE-1 and CE-2

Comparative Examples 1 and 2 (CE-1 and CE-2) were prepared as described in Example-1, using Tegaderm™ Film (Transparent Film Dressing 1624W, 3M Company, St. Paul, Minn.) and a silicone elastomer (HT6240, Stockwell Elastomerics, Inc., Philadelphia, Pa.) in place of Viscoelastic Backing 1, respectively.

Comparative Example CE-3—Wound Closure Dressing System Comprising Fully-Stretched Viscoelastic Backing 2

Two strips of acrylic adhesive, 1.75 cm wide by 20 cm long, and 0.0025 inches thick were laminated to one surface of a piece of Viscoelastic Backing 2 (20 cm×10 cm) such that the strips were parallel and separated by 0.5 cm. Pieces were cut from this laminate 3.5 cm wide and 10 cm long. One end of this film was clamped to a bench with the adhesive layers facing up. The release liners were both removed. The other end was then taped to a stainless steel coupon, and the whole film was stretched until the most distant edges of the adhesive strips were about 8 cm apart. A 5 cm×10 cm polypropylene sheet was then placed on the backing while maintaining the manual stretch. The excess backing without adhesive coating on each edge was trimmed off to leave a stretched dressing 8 cm long and less than 3.5 cm wide with a stretch ratio of 100% over the entire area of the dressing. A strip of polyester tape (5 cm wide) was then wrapped around both faces of the assembly in the same direction as the direction of stretching (i.e., along the strain axis) to form a complete wrap around both faces of the assembly. The strip of polyester tape provided a first portion of a support for the system, and the polypropylene sheet provided a second portion of the support.

Results

Backing Recovery

Viscoelastic backings 1 and 2, as well as the Comparative Examples were tested for Recovery with the results shown in Table 2.

TABLE 2

Backing Recovery

| Backing | Recovery at 10 seconds | Recovery at 48 hours |
|---|---|---|
| Viscoelastic Backing 1 | 27% | 100% |
| Viscoelastic Backing 2 | 39% | 99% |
| Viscoelastic Backing 3 | 38% | 100% |
| CE-1: Tegaderm Film | 87% | 99% |
| CE-2: Silicone Elastomer | 99% | 100% |

TABLE 3

Recovery on Skin

| Example | Middle Section % Elongation | Middle Section Recovery at application (%) | Middle Section Recovery at 4 min. (%) | Middle Section Recovery at 20 min. (%) |
|---|---|---|---|---|
| Example 2 | 100% | 33% | 87% | 93% |
| Example 3 | 50% | 38% | 88% | 88% |
| Example 4 | 100% | 40% | 87% | 93% |

Recovery on Simulated Wound using Example-1

Figure 16A:
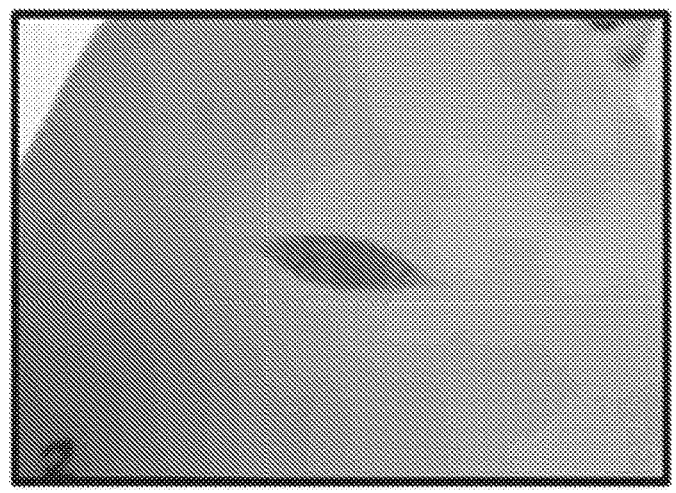
FIG. 16A is a photographic image of a simulated wound used in the Examples.
Figure 16B:
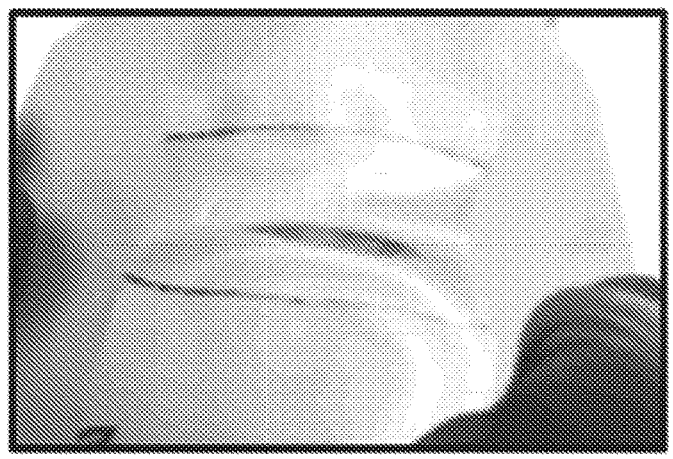
FIGS. 16B-16C are photographic images of the wound closure dressing of Example 1 applied to the simulated wound of FIG. 16A, at about 60 seconds after application (FIG. 16B), and at about 3 min. after application (FIG. 16C), as described in the Examples.
Figure 16C:
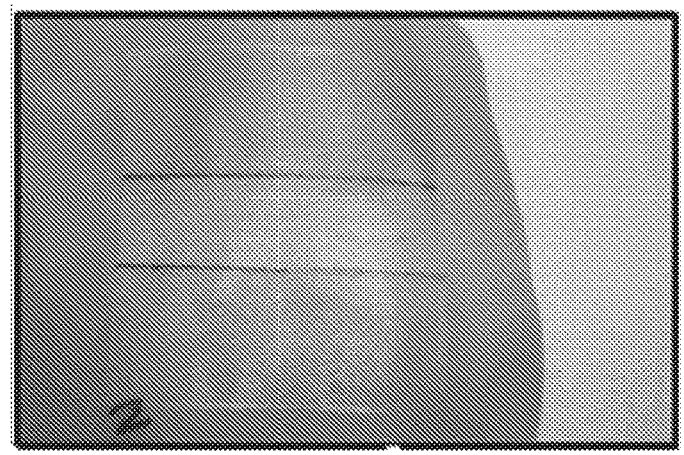

The wound closure dressing of Example 1 was decoupled from the support and placed over a simulated wound. The simulated would was an incision approximately 2.5 cm long and 0.3 cm wide though the skin of a sacrificed hairless guinea pig. FIGS. 16A-16C are images of the wound before the application of Example 1 (FIG. 16A), approximately 60 seconds after application (FIG. 16B), and approximately 3 minutes after application (FIG. 16C). In FIG. 16C, the wound had closed, and the ink lines on the backing had decreased from their initial stretched state (2.5 cm) to approximately 1.6 cm, representing a 73% recovery of the middle section (i.e., (2.5 cm−1.6 cm)/(2.5 cm−1.27 cm)×100=73%).

Adhesion Test Results

To characterize the adhesive performance of the skin contact adhesive used in Examples 1-5, the 180° Peel Test Method was used with the acrylic adhesive on a stainless steel substrate, and the average peel strength was 2.8 N/cm.

To characterize the adhesive performance of the antibacterial gel pad from Example 4, the 180° Peel Test Method was used with the antibacterial gel pad (0.02 to 0.03 mm thick) on a stainless steel substrate, and the average peel strength was 1.9 N/cm.

The characterize the adhesive performance of the skin contact adhesive against the support material used in Example 1-5, the 180° Peel Test Method was used with the acrylic adhesive on a polypropylene sheet substrate, and the average peel strength was 1.7 N/cm.

Skin Irritation Results

Example 6 and Comparative Example CE-3 were tested according to the Skin Irritation test method.

One dressing from Example 6 was removed from the polypropylene sheet and immediately applied to one side of the back of a hairless guinea pig with no manually applied tension. One dressing from Comparative Example CE-3 was similarly applied to the other side of the same animal's back with no manually applied tension.

Figure 17A:
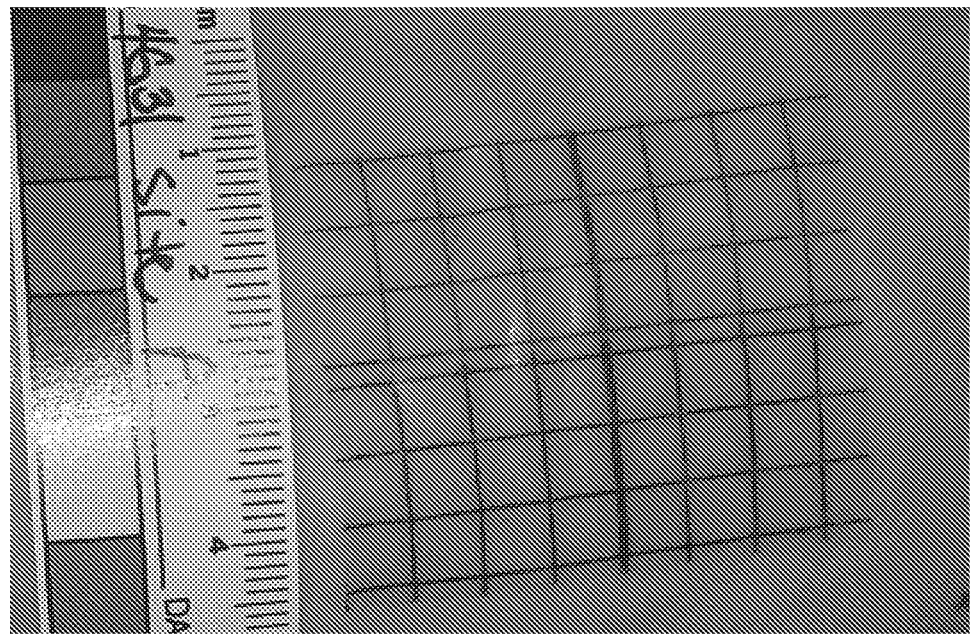
FIGS. 17A and 17B are photographic images of the wound closure dressing of Example 6 and Comparative Example CE-3, respectively, after 24 hours of being applied to healthy skin of hairless guinea pigs, according to the Skin Irritation test method, as described in the Examples.
Figure 17B:
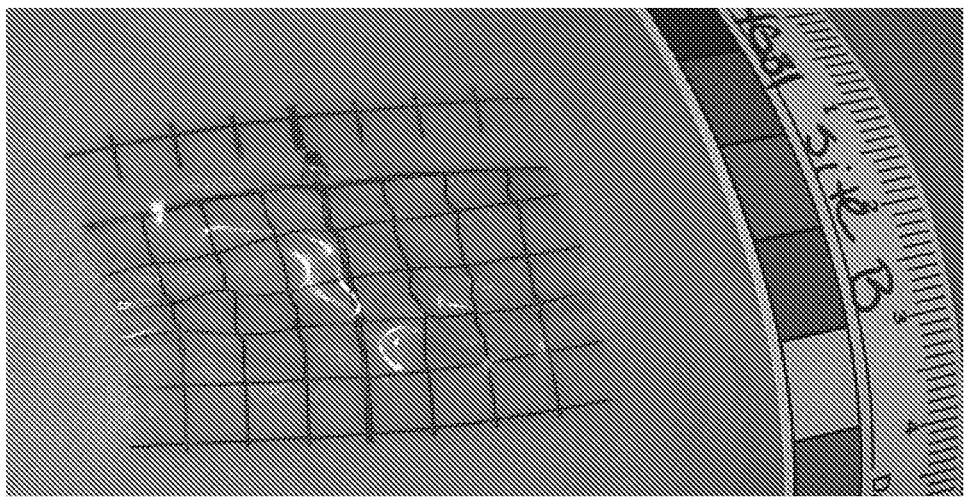
Figure 18A:
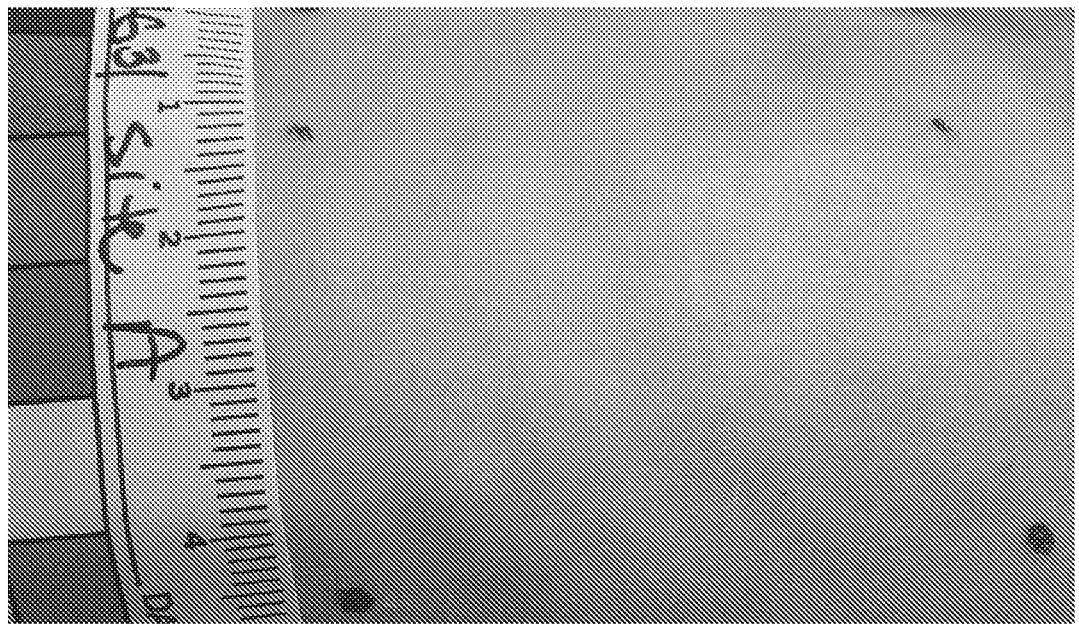
FIGS. 18A and 18B are photographic images of the pig skin after removal of Example 6 and Comparative Example CE-3, respectively, according to the Skin Irritation test method, as described in the Examples.
Figure 18B:
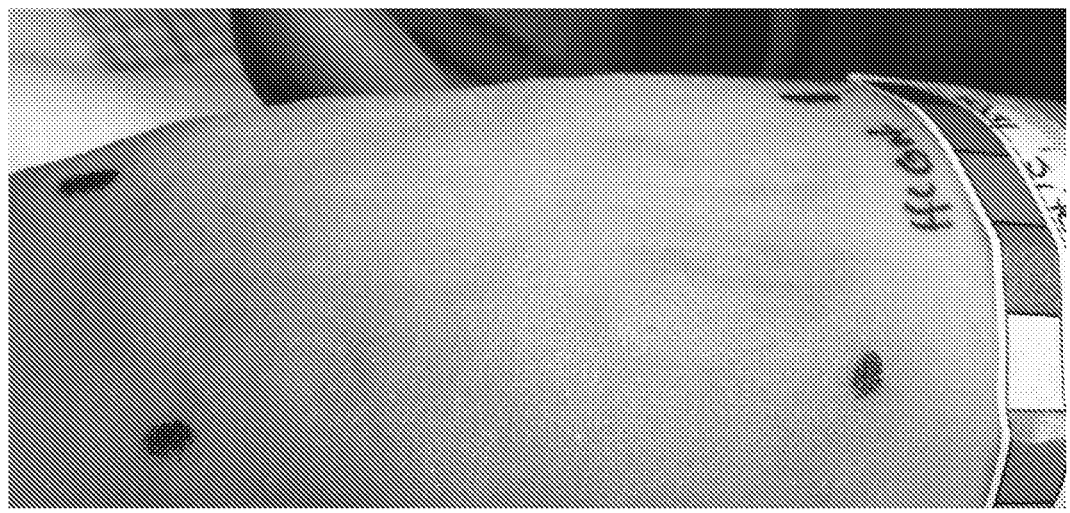

After 24 hours, Example 6 was generally flat (FIG. 17A), but Comparative Example CE-3 was severely wrinkled (FIG. 17B). Following removal of the dressings from the skin, the skin under Example 6 appeared healthy and generally un-affected by the dressing (FIG. 18A). The skin under Comparative Example CE-3 showed marks where the wrinkled dressing had deformed the skin, and areas of redness suggested skin irritation (FIG. 18B).

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A wound closure dressing system comprising:
a support assembly; and
a viscoelastic backing in a pre-stretched configuration,
the viscoelastic backing comprising a first major surface configured to face skin when in use, a first end, a second end, and a middle section located between the first end and the second end, wherein only the middle section of the viscoelastic backing is in the pre-stretched configuration, and
wherein the viscoelastic backing recovers, at room temperature:
no more than 40% of its deformation after 10 seconds, after being strained to 50% elongation for 30 minutes, and
at least 70% of its deformation after 48 hours, after being strained to 50% elongation for 30 minutes; and
a skin-contact adhesive on the first major surface of the viscoelastic backing at the first end and the second end,
wherein more than 50% of the first major surface of the middle section is free of the skin-contact adhesive,
wherein the viscoelastic backing is coupled to the support assembly via the skin-contact adhesive only.

2. The wound closure dressing system of claim 1, wherein the viscoelastic backing recovers, at room temperature:
no more than 30% of its deformation after 10 seconds, after being strained to 50% elongation for 30 minutes.

3. The wound closure dressing system of claim 1, wherein the viscoelastic backing recovers, at room temperature:
at least 90% of its deformation after 48 hours, after being strained to 50% elongation for 30 minutes.

4. The wound closure dressing system of claim 1, wherein:
the first end is configured to be secured to skin on one side of a wound site;
the second end is configured to be secured to skin on an opposite side of the wound site from the first end; and
the middle section is configured to be positioned over the wound site.

5. The wound closure dressing system of claim 1, wherein the skin-contact adhesive is patterned on the first major surface of the middle section.

6. The wound closure dressing system of claim 1, further comprising an absorbent layer coupled to the first major surface of the middle section of the viscoelastic backing.

7. The wound closure dressing system of claim 6, wherein the absorbent layer includes at least one of a hydrogel and a foam.

8. The wound closure dressing system of claim 6, wherein the absorbent layer is positioned adjacent a lateral side of the middle section of the viscoelastic backing.

9. The wound closure dressing system of claim 1,
wherein the wound closure dressing is coupled to the support assembly with the viscoelastic backing in the pre-stretched configuration, such that the pre-stretched configuration of the viscoelastic backing is maintained until the wound closure dressing is decoupled from the support assembly.

10. The wound closure dressing system of claim 9, wherein the support assembly rigid relative to the viscoelastic backing.

11. The wound closure dressing system of claim 9, wherein the support assembly is configured to be coupled to the first major surface of the viscoelastic backing, and configured to be coupled to a second major surface opposite the first major surface of at least the middle section of the viscoelastic backing.

12. The wound closure dressing system of claim 1, wherein the wound closure dressing is further coupled to the support assembly via an overwrap that is positioned around at least a portion of the wound closure dressing and the support assembly.

13. The wound closure dressing system of claim 1, wherein the wound closure dressing is further coupled to the support assembly via a fastener.

14. A wound closure dressing kit comprising:
a first wound closure dressing system according to claim 1, wherein the viscoelastic backing of the first wound closure dressing is pre-stretched by a first percent elongation; and
a second wound closure dressing system according to claim 1, wherein the viscoelastic backing of the second wound closure dressing is pre-stretched by a second percent elongation that is less than the first percent elongation.

* * * * *

UNITED STATES PATENT AND TRADEMARK OFFICE
CERTIFICATE OF CORRECTION

PATENT NO. : 10,973,692 B2
APPLICATION NO. : 15/533733
DATED : April 13, 2021
INVENTOR(S) : Joseph Douglas Rule It is certified that error appears in the above-identified patent and that said Letters Patent is hereby corrected as shown below:

In the Specification

Column 5,
Line 14 (approx.), delete "2" and insert -- 102 --, therefor.

Signed and Sealed this
Thirty-first Day of January, 2023

*Katherine Kelly Vidal*

Katherine Kelly Vidal
*Director of the United States Patent and Trademark Office*